United States Patent
Long et al.

(10) Patent No.: US 7,435,801 B2
(45) Date of Patent: Oct. 14, 2008

(54) ANTIBODIES AND OTHER LIGANDS DIRECTED AGAINST KIR2DL4 RECEPTOR FOR PRODUCTION OF INTERFERON GAMMA

(75) Inventors: Eric O. Long, Rockville, MD (US); Sumati Rajagopalan, Bethesda, MD (US)

(73) Assignee: The United States of America, as represented by the Department of Health and Human Services, Washington, DC (US)

( * ) Notice: Subject to any disclaimer, the term of this patent is extended or adjusted under 35 U.S.C. 154(b) by 677 days.

(21) Appl. No.: 10/420,067

(22) Filed: Apr. 18, 2003

(65) Prior Publication Data

US 2003/0232051 A1    Dec. 18, 2003

Related U.S. Application Data

(63) Continuation of application No. PCT/US01/46098, filed on Oct. 23, 2001.

(60) Provisional application No. 60/242,419, filed on Oct. 23, 2000.

(51) Int. Cl.
C12P 21/08 (2006.01)
C07K 16/00 (2006.01)
C12N 5/00 (2006.01)

(52) U.S. Cl. .............................. 530/388.73; 530/387.3; 530/388.1; 435/346

(58) Field of Classification Search .................. None
See application file for complete search history.

(56) References Cited

OTHER PUBLICATIONS

Welch et al., 2003, immunogenetics, vol. 54: 782-790.*
Cleland et al., 1993, Critical Reviews in Therapeutic Drug Carrier Systems< vol. 10: 307-377.*
Campbell et al., 1984, Monoclonal Antibody Technology, pp. 1-32.*
Lazar et al., 1988, Mol. Cell. Biol. vol. 8: 1247-1252.*
Whisstock et al., 2003, Quaterly Reviews of Biophysics, vol. 36: 307-340.*
Mikayama et al., 1993, PNAS, vol. 90: 10056-10060.*
Burgess et a., 1990, J. Cell. Biol. vol. 111: 2129-2138.*
Gavilondo et al., Jul. 2000, Biotechniques, vol. 29: 128-145.*
Ashkar, A.A. et al. 2000 Interferon contributes to initiation of uterine vascular modification, decidual integrity, and uterine natural killer cell maturation during normal murine pregnancy. *J. Exp. Med.* 192:259-269.
Biron, C.A. et al. 1999 Natural killer cells in antiviral defense: Function and regulation by innate cytokines. *Annu. Rev. Immunol.* 17:189-220.
Cantoni, C. et al. 1998 p49, a putative HLA class I-specific inhibitory NK receptor belonging to the immunoglobulin superfamily. *Eur. J. Immunol.* 28:1980-1990.
Cooper, M.A. et al. 2001 Human natural killer cells; a unique innate immunoregulatory role for the CD56bright subset. *Blood* 97:3146-3151.
Hershberger, K.L. et al. 2001 Diversity of the killer cell Ig-like receptors of rhesus monkeys. *J. Immunol.* 166:4380-4390.
Khakoo, S.I. et al. 2000 Rapid evolution of NK cell receptor systems demonstrated by comparison of chimpanzees and humans. *Immunity* 12:687-698.
Lanier, L.L. 1998 NK cell receptors. *Annu. Rev. Immunol.* 16:359-393.
Lanier, L. L. 2001 On guard-activating NK cell receptors. *Nat. Immunol.* 2:23-27.
Loke, Y.W., A. King. 1997 Immunology of human placental implantation: clinical implications of our current understanding. *Mol. Med. Today* 3:153-159.
Long, E.O., S. Rajagopalan 2000 HLA class I recognition by killer cell Ig-like receptors. *Semin. Immunol.* 12:101-108.
Mainiero, F. et al. 2000 RAC1/P38 MAPK signaling pathway controls 1 integrin-induced interleukin-8 production in human natural killer cells. *Immunity* 12:7-16.
Moretta, A. et al. 2000 Natural cytotoxicity receptors that trigger human NK-cell-mediated cytolysis. *Immunol. Today* 21:228-234.
Perussia, B. 2000 Signaling for cytotoxicity. *Nat. Immunol.* 1:372-374.
Ponte, M. et al. 1999 Inhibitory receptors sensing HLA-G1 molecules in pregnancy: decidua-associated natural killer cells express LIR-1 and CD94/NKG2A and acquire p49, an HLA-G1-specific receptor. *PNAS USA* 96:5674-5679.
Rajagopalan S. et al. 2001 Cutting edge: induction of IFN-gamma production but not cytotoxicity by the killer cell Ig-like receptor KIR2DL4 (CD158d) in resting NK cells. *J Immunol.* 167(4):1877-1881.
Rajagopalan, S., E.O. Long. 1999 A human histocompatibility leukocyte antigen (HLA)-G-specific receptor expressed on all natural killer cells. *J. Exp. Med.* 189:1093-1099.
Rincon, M. et al. 1998 Interferon- expression by Th1 effector T cells mediated by the p38 MAP kinase signaling pathway. *EMBO J.* 17:2817-2829.
Selvakumar, A. et al. 1996 NK cell receptor gene of the KIR family with two Ig domains but highest homology to KIR receptors with three Ig domains. *Tissue Antigens* 48:285-295.
Trotta, R. et al. 1998 Dependence of both spontaneous and antibody-dependent, granule exocytosis-mediated NK cell cytotoxicity on extracellular signal-regulated kinases. *J. Immunol.* 161:6648-6656.

(Continued)

*Primary Examiner*—G. R. Ewoldt
*Assistant Examiner*—Amy Juedes
(74) *Attorney, Agent, or Firm*—Knobbe, Martens, Olson & Bear, LLP

(57) ABSTRACT

The present invention provides antibodies and other ligands that specifically bind to KIR2DL4 receptor and stimulate production of interferon gamma. One embodiment is mAb #33 on deposit at ATCC.

17 Claims, 10 Drawing Sheets

OTHER PUBLICATIONS

Valiante, N.M., G. Trinchieri 1993 Identification of a novel signal transduction surface molecule on human cytotoxic lymphocytes. *J. Exp. Med.* 178:1397-1406.

Valiante, N.M. et al. 1997 Functionally and structurally distinct NK cell receptor repertoires in the peripheral blood of two human donors. *Immunity* 7:739-751.

Watzl, C. et al. 2000 Cutting edge: NK cell inhibitory receptors prevent tyrosine phosphorylation of the activation receptor 2B4 (CD244). *J. Immunol.* 165:3545-3548.

Yang, J. et al. 2001 IL-18-stimulated GADD45 is required in cytokine-induced, but not TCR-induced, IFN-production. *Nat. Immunol.* 2:157-164.

Yu, T K. et al. 2000 IL-2 activation of NK cells: involvement of MKK1/2/ERK but not p38 kinase pathway. *J. Immunol.* 164:6244-6251.

Rajagopalan, S., E.O. Long. (*erratum*) J Exp Med Jun. 5, 2000; 191 (11) : A Human Histocompatiblity Leukocyte Antigen (HLA)-G-specific Receptor Expressed on All Natural Killer Cells J. Exp. Med. 189 (7):1093-1099.

* cited by examiner

ANTIBODIES AND OTHER LIGANDS DIRECTED AGAINST KIR2DL4 RECEPTOR FOR PRODUCTION OF INTERFERON GAMMA

RELATED APPLICATIONS

This application is a continuation and claims the benefit of priority of International Application No. PCT/US01/46098 filed Oct. 23, 2001, designating the United States of America and published in English, which claims the benefit of priority of U.S. Provisional Application No. 60/242,419 filed Oct. 23, 2000, both of which are hereby expressly incorporated by reference in their entireties.

FIELD OF THE INVENTION

The present invention relates to the field of molecular biology. The present invention provides antibodies and other ligands that specifically bind to KIR2DL4 receptor and stimulate production of interferon gamma. One embodiment is mAb #33 on deposit at ATCC.

BACKGROUND OF THE INVENTION

Interferons are one of the body's natural defensive responses to foreign components such as microbes, tumors, and antigens. Interferons have potent antiproliferative and immune-regulatory activity. Interferon gamma (IFN-gamma), one of three major classes of interferons, is a potent anti-viral and anti-microbial substance produced by certain white blood cells. One of the most efficient producers of interferon gamma is a natural killer (NK) cell. NK cells are activated during infections by viruses and by other intracellular pathogens, such as parasites and bacteria. Soluble substances, such as interleukins, produced by infected cells activate NK cells to secrete interferon gamma. Injection of interleukins into patients to stimulate NK cells has not been a successful therapeutic approach because of the toxicity involved.

SUMMARY OF THE INVENTION

Human natural killer cells express an array of killer cell Ig-like receptors (KIR) that recognize major histocompatibility complex (MHC) molecules on target cells. The outcome of this interaction is either activation or inhibition of NK function (e.g., cytotoxicity, IFN-gamma release) depending on the integration of positive and negative signals coming from these receptors. We describe a structurally unique KIR family member, KIR2DL4, that shares features with both activating and inhibitory receptors. While its long cytoplasmic tail contains an immunoreceptor tyrosine-based inhibition motif (ITIM), suggesting inhibitory potential, its transmembrane region contains a positively charged amino acid that is typical of KIR with activatory potential. In contrast to other KIR that are clonally distributed, KIR2DL4 is expressed by all NK cells. We produced monoclonal antibodies (mAbs) against KIR2DL4 and show that crosslinking KIR2DL4 on the surface of human NK cell lines and populations results in the triggering of lytic function and IFN-gamma production. We further show that this activating potential of KIR2DL4 is controlled by amino acids in its transmembrane domain. Vaccinia virus mediated gene transfer of mutant KIR2DL4 with two amino acid changes in the transmembrane region resulted in the loss of lytic function and led to the inhibition of lysis of target cells by NK populations. Finally we show that in freshly isolated, resting NK cells, there is an uncoupling of lytic function and IFN-gamma production. Engagement of KIR2DL4 on resting NK cells results in striking levels of IFN-gamma production in the absence of any appreciable lytic activity. The production of IFN-gamma by resting NK cells in response to KIR2DL4 engagement is relevant to various therapeutic applications.

DEPOSIT OF MICROORGANISMS

Figure 1:
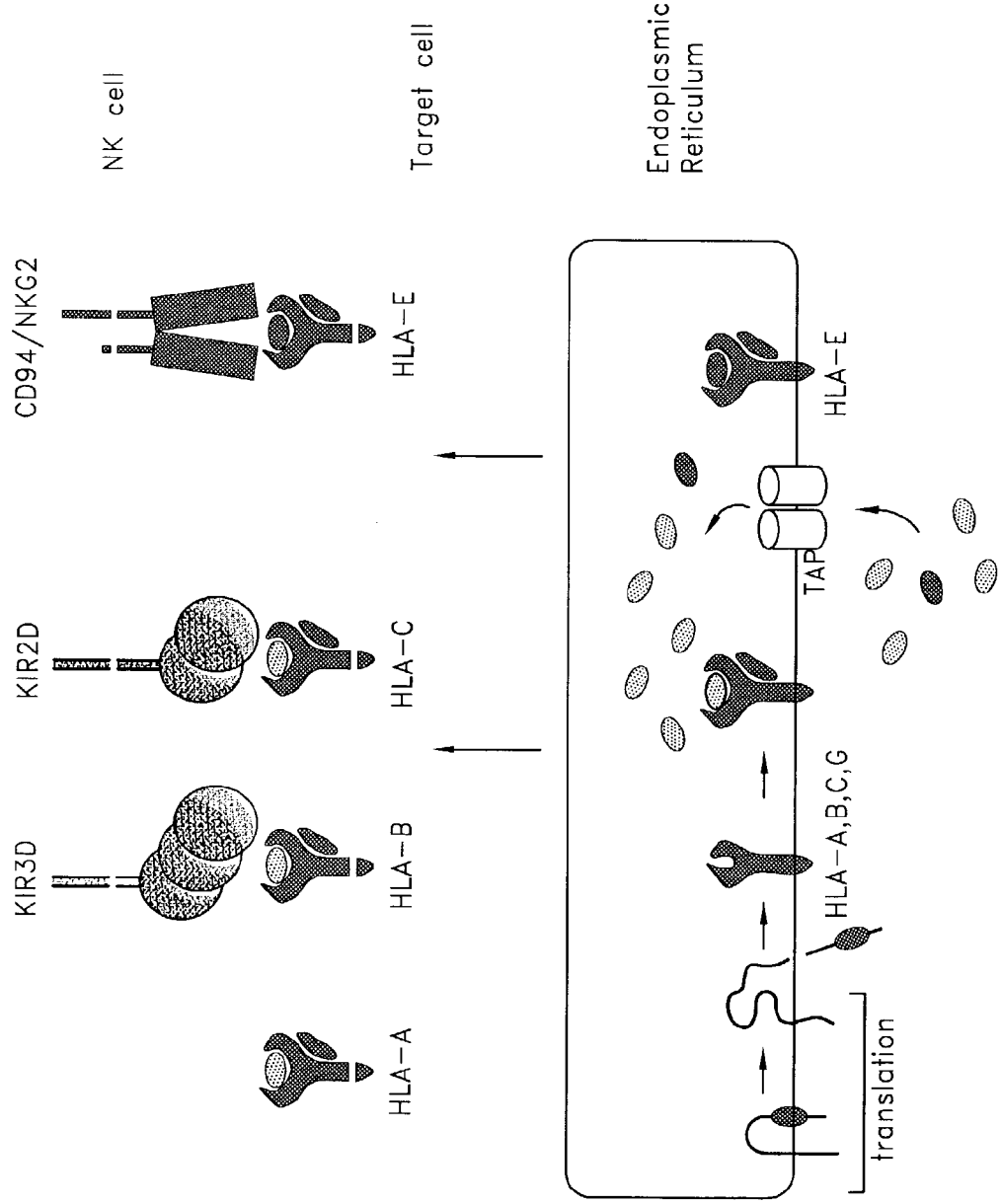
FIG. 1. Recognition of HLA molecules. Peptide-loaded classical major histocompatibility complex (MHC) class I molecules such as human leukocyte antigen (HLA)-B and HLA-C are recognized by killer cell Ig-like receptors (KIR). In contrast, the non-classical HLA-E depends on the expression of other MHC class I molecules for its expression since it uses their signal sequences as the only source of peptide. HLA-E molecules are recognized by the lectin like CD94/NKG2 receptors.

The following microorganism has been deposited in accordance with the terms of the Budapest Treaty with the American Type Culture Collection (ATCC), Manassas, Va., on the date indicated:

| Microorganism | Accession No. | Date |
| --- | --- | --- |
| Mouse B Cell Hybridoma #33-8 | PTA-2594 | Oct. 13, 2000 |

Cells are grown in Dulbecco's Modified Eagle's Medium containing 10% fetal calf serum. Store deposit at −80° C. B Cell Hybridoma produces IgG1 monoclonal antibodies against KIR2DL4. Mouse B Cell Hybridoma #33-8 was deposited as ATCC Accession No. PTA-2594 on Oct. 13, 2000 with the American Type Culture Collection (ATCC), 10801 University Blvd., Manassas, Va. 20110-2209, USA. This deposit was made under the provisions of the Budapest Treaty on the International Recognition of the Deposit of Microorganisms for the Purposes of Patent Procedure and the Regulations thereunder (Budapest Treaty). This assures maintenance of a viable culture of the deposit for 30 years from date of deposit. The deposit will be made available by ATCC under the terms of the Budapest Treaty, and subject to an agreement between Applicant and ATCC which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14). Availability of the deposited strain is not to be construed as a license to practice the invention in contravention of the rights granted under the authority of any government in accordance with its patent laws.

DETAILED DESCRIPTION OF THE PREFERRED EMBODIMENT

The present invention is based on the surprising discovery that a receptor protein (called KIR2DL4), expressed by all natural killer (NK) cells, stimulates NK cells to produce interferon gamma. A monoclonal antibody to the receptor was produced (#33) that can be used to stimulate interferon gamma (IFN-gamma) production without any other stimulus. The possibility of inducing interferon gamma production in the absence of toxic side effects associated with administration of interleukins is a medical benefit. Interferon gamma is an effective therapy for various types of infections, cancers, and autoimmune diseases. In addition, interferon gamma plays an important role in the establishment of a proper implantation site for the fetus during early pregnancy and may be used as an infertility treatment. Alternatively, there may exist pathologies in which interferon gamma production induced by the interaction of KIR2DL4 with its natural ligand is a contributing factor. For example, chronic interferon gamma production in the epidermis is one of the manifestations of psoriasis, a common disease of the skin. Antibodies or compounds that interfere with the binding of KIR2DL4 to its natural ligand but without acting as agonists are envisioned as being useful to prevent interferon gamma production.

The findings indicate:

Cross-linking KIR2DL4 with a specific mAb on IL-2-activated peripheral blood NK cells resulted in both activation of lysis and IFN-gamma production.

An intact transmembrane domain including an arginine-tyrosine sequence is necessary for the activating function of KIR2DL4.

Engagement of KIR2DL4 in resting NK cells results in striking levels of IFN-gamma production in the absence of any appreciable cytotoxic activity. Other activation receptors (e.g., CD16, 2B4) did not induce comparable IFN-gamma release. Thus, KIR2DL4 is envisioned as having an important role in initiating a response by resting NK cells.

HLA-G expressed by fetal trophoblast cells at the maternal fetal interface is a ligand for KIR2DL4. Therefore, KIR2DL4 is envisioned as providing useful signals to decidual NK cells during pregnancy.

The present invention encompasses the use of antibodies and other ligands directed against KIR2DL4 receptor for the purpose of modulating, i.e., stimulating or inhibiting, the production of interferon gamma. In particular, the invention encompasses agonists and antagonists to KIR2DL4 receptor, including small molecules, large molecules, wild-type ligands and mutant ligands, and antibodies and its fragments, as well as nucleotide sequences encoding these compositions.

Further, the present invention relates to methods for the use of KIR2DL4 receptor (or its nucleotide sequence) for the identification of compounds that modulate, i.e., act as agonists or antagonists, of KIR2DL4 gene expression or KIR2DL4 gene product activity.

Still further, the present invention encompasses methods and compositions to ameliorate various diseases, infections, and tumors responsive to interferon gamma. By way of example and not limitation, examples of such diseases, infections, and tumors are: idiopathic pulmonary fibrosis, leukemia, lymphoma, melanoma, kidney cancer, endometrial cancer, chronic granulomatosis, rheumatoid arthritis, scleroderma, hepatitis B, hepatitis C, viral enteritis, herpes and tuberculosis. The present invention is additionally useful as an anti-infective agent, including antiviral, anti-bacterial, and anti-parasitic activities. The present invention is also envisioned as being effective to treat infertility. Alternatively, the present invention encompasses methods and compositions to ameliorate various pathologies in which interferon gamma production induced by the interaction of KIR2DL4 with its natural ligand is a contributing factor.

Induction of IFN-gamma Production but Not Cytotoxicity by the Killer Cell Ig-Like Receptor KIR2DL4 in Resting NK Cells Activated natural killer (NK) cells lyse tumor cells and virus-infected cells and produce interferon gamma (IFN-gamma) upon contact with sensitive target cells. The regulation of these effector responses in resting NK cells is not well understood. We now describe a receptor, KIR2DL4, that has the unique property of inducing IFN-gamma production, but not cytotoxicity, by resting NK cells in the absence of cytokines. In contrast, the NK cell-activation receptors CD16 and 2B4 induced cytotoxicity but not IFN-gamma production. The induction by KIR2DL4 of IFN-gamma production by resting NK cells was blocked by an inhibitor of the p38 mitogen-activated protein kinase (MAPK) signaling pathway, in contrast to the IL-2-induced IFN-gamma secretion that was sensitive to inhibition of the extra-cellular signal-regulated kinase mitogen-activated protein kinase (Erk MAPK) pathway. These results reveal a functional dichotomy (cytokine production vs. cytotoxicity) in the response of resting NK cells, as dictated by the signals of individual receptors.

The signals that convert a circulating NK cell from a resting to a more activated, cytokine-secreting, and lytic mode in vivo are not fully understood. Although resting NK cells are clearly activated by certain cytokines and chemokines (including IL-2 and IL-12) to become cytotoxic and to secrete IFN-gamma (Biron C. A. et al. 1999 *Annu Rev Immunol* 17:189), it is unclear which receptors contribute to activation of resting NK cells upon contact with target cells and whether independent signals can uncouple the induction of cytokine production from a cytotoxic response. The interaction of activated NK cells with target cells can induce cytotoxicity and IFN-gamma production, depending on the outcome of signals from activating and inhibitory receptors (Lanier, L. L. 1998 *Annu Rev Immunol* 16:359; Moretta, A. et al. 2000 *Immunol Today* 21:228; Lanier, L. L. 2001 *Nature Immunol* 2:23).

Target cell lysis can be induced by Ab-dependent cellular toxicity through CD16 or by activation receptors such as NKp46, 2B4 (CD244), and others. Human NK cells express killer cell Ig-like receptors (KIR) and lectin-like receptors (CD94/NKG2) that recognize MHC class I ligands and either inhibit or activate NK cytotoxicity (Long, E. O. and S. Rajagopalan 2000 *Semin Immunol* 12:101). Inhibitory receptors have immunoreceptor tyrosine-based inhibition motifs (ITIMs) in their cytoplasmic tails, whereas activating receptors lack the ITIM and pair with the immunoreceptor tyrosine-based activation motif (ITAM)-containing signaling partner DAP12 via charged amino acids in the transmembrane region (Lanier, L. L. 2001 *Nature Immunol* 2:23).

KIR2DL4, (also referred to as 2DL4) is a KIR family member (recently designated CD158d) that shares structural features with both activating and inhibitory receptors (Selvakumar, A. et al. 1996 *Tissue Antigens* 48:285). 2DL4 has a cytoplasmic ITIM, suggesting inhibitory function, and a positively charged amino acid in the transmembrane region, a feature typical of activating KIR. Unlike other clonally distributed KIRs, 2DL4 is transcribed by all NK cells (Valiante, N. M. et al. 1.997 *Immunity* 7:739; Cantoni, C. et al. 1998 *Eur J Immunol* 28:1980; Rajagopalan, S. and E. O. Long. 1999 [published erratum appears in *J Exp Med* 2000 191:2027] *J Exp Med* 189:1093). In this disclosure, we show that 2DL4 is an activating receptor with the unique property of inducing IFN-gamma production but not cytotoxicity in resting NK cells.

The mAbs, Cells, and Reagents.

BALB/c mice were immunized i.p. five times with $5 \times 10^6$ NK3.3 cells and boosted once with 50 μg 2DL4-Ig fusion protein. Supernatants of hybridomas produced by fusion with P3×63Ag8 were screened by ELISA with 2DL4-Ig fusion protein (Rajagopalan, S. and E. O. Long. 1999 [published erratum appears in *J Exp Med* 2000 191:2027] *J Exp Med* 189:1093). Positive hybridomas were further tested by flow cytometry on NK3.3 cells. Three hybridomas were obtained after subcloning: 33 (IgG1), 36 (IgM), and 64 (IgM). The hemagglutinin (HA)-tag specific Abs (Covance, Richmond, Calif.) used were mAb 16B 12 (IgG 1) and polyclonal rabbit Ab HA.11. The mAbs directed against NK surface proteins were 2B4 (C1.7, IgG1; Beckman Coulter, Miami, Fla.); CD94 (HP3D9, IgG1; Ancell, Bayport, Minn.), and CD16 (3G8, IgG1; Medarex, Princeton, N.J.). Isotype-matched control Abs for IgG1, IgG2a and IgM were obtained from Beckman Coulter. The following NK cell lines were used: NK92 (obtained from H. Klingemann, Rush University, Chicago, Ill.), NK3.3 (obtained from J. Kornbluth, St. Louis University School of Medicine, St. Louis, Mo.), and NKL (obtained from M. J. Robertson, Indiana University Cancer Research Institute, Indianapolis, Ind.). 293T/17 and P815 cells were obtained from American Type Culture Collection (Manassas, Va.). Human NK cell populations were derived from the peripheral blood lymphocytes (PBL) of normal donors as previously described (Watzl, C. et al. 2000 *J Immunol* 165:3545) using the MACS NK cell isolation kit (Miltenyi Biotec, Auburn, Calif.). Freshly isolated NK cells cultured in Iscove's medium containing 10% human serum without any added cytokines were used within 24 h. NK cells were expanded in the presence of IL-2 as previously described (Watzl, C. et al. 2000 *J Immunol* 165:3545).

Molecular Construct Transfections and Immunoblotting.

The 2DL4 cDNA cloned into pBlueScript was used as a PCR template using the following primers: sense primer (containing a BglII site), 5'-GGGGAGATCT-CACGTGGGTGGTCAGGACAA-3' (SEQ ID NO: 1); and antisense primer (containing SalI and NheI sites), 5'-GACTGGTCGACGCTAGCTCAGATTC-CAGCTGCTGGTA-3' (SEQ ID NO: 2), and cloned into the BglII and SalI sites of pDisplay in frame with a signal sequence and a HA tag (Invitrogen, Carlsbad, Calif.). To produce the HA-2DL4 (RY-GT) mutant, the pDisplay-HA-2DL4 was mutated using the QuikChange kit (Stratagene, La Jolla, Calif.). Primers used were: sense, 5'-CATGCTGTGAT-TGGGACCTCAGTGGCCATC-3' (SEQ ID NO: 3); and antisense, 5'-GATGGCCACTGAGGTCCCAATCACAG-CATG-3' (SEQ ID NO: 4). Wild-type and mutant HA-2DL4 were cloned using KpnI and NheI into the vaccinia virus vector pSC65 with a modified polylinker, and recombinant viruses were produced as previously described (Rajagopalan, S. and E. O. Long. 1999 [published erratum appears in *J Exp Med* 2000 191:2027] *J Exp Med* 189:1093). All constructs were verified by sequencing. The 293 T/17 cells were transiently transfected using LipofectAMINE (Life Technologies). After 48 h, cells were lysed in 0.3% 3-[(3-cholami-dopropyl)dimethylammonio]-1-propanesulfonate (CHAPS), 20 mM Tris-HCl (pH 7.4), 150 mM NaCl, 1 mM PMSF, and 8 mM iodoacetamide. Samples were either used as total lysate or immunoprecipitated with mAbs followed by protein G agarose (Life Technologies). Western blotting was done as previously described (Watzl, C. et al. 2000 *J Immunol* 165: 3545), and blots were developed using rabbit anti-HA Abs (Covance, Richmond, Calif.), followed by goat anti-rabbit IgG peroxidase (Amersham, Arlington Heights, Ill.) and Super Signal substrate (Pierce, Rockford, Ill.).

Functional Assays with NK Cells.

NK cells ($5 \times 10^5$/well) were co-cultured with or without P815 cells ($1 \times 10^5$/well) for 20 h with mAbs as indicated. Culture supernatants were tested for IFN-gamma production by ELISA (R&D Systems, Minneapolis, Minn.). In parallel, NK cells were also tested for cytotoxicity against P815 cells in a 3-h $^{51}$Cr-release assay. Purified vaccinia viruses were used to infect IL-2-activated NK cells as previously described (Rajagopalan, S., and E. O. Long. 1999 [published erratum appears in *J Exp Med* 2000 191:2027] *J Exp Med* 189:1093). After infection with 10 PFU/cell of each virus for 1.5 h, cells were washed and either monitored for receptor expression by flow cytometry or plated for standard 3-h $^{51}$Cr-release assays using P815 target cells. Treatment of NK cells with the extracellular signal-regulated (ERK) kinase (MEK)1 inhibitor PD098059 (Calbiochem, La Jolla, Calif.) or the p38 mitogen-activated protein kinase (MAPK) inhibitor SB203580 (Sigma-Aldrich, St. Louis, Mo.) was for 1-2 h at 37° C. before addition of Abs or rIL-2 (5 U/ml). Inhibitors were present during stimulation with mAbs. Negative controls contained as much DMSO as the highest concentration of inhibitor. The inhibitors did not interfere with NK cell viability as assessed by trypan blue exclusion. After 20 h, culture supernatants were tested for IFN-gamma by ELISA.

2DL4 Induces Cytotoxicity by Activated NK Cells but not by Resting NK Cells.

Figure 4:
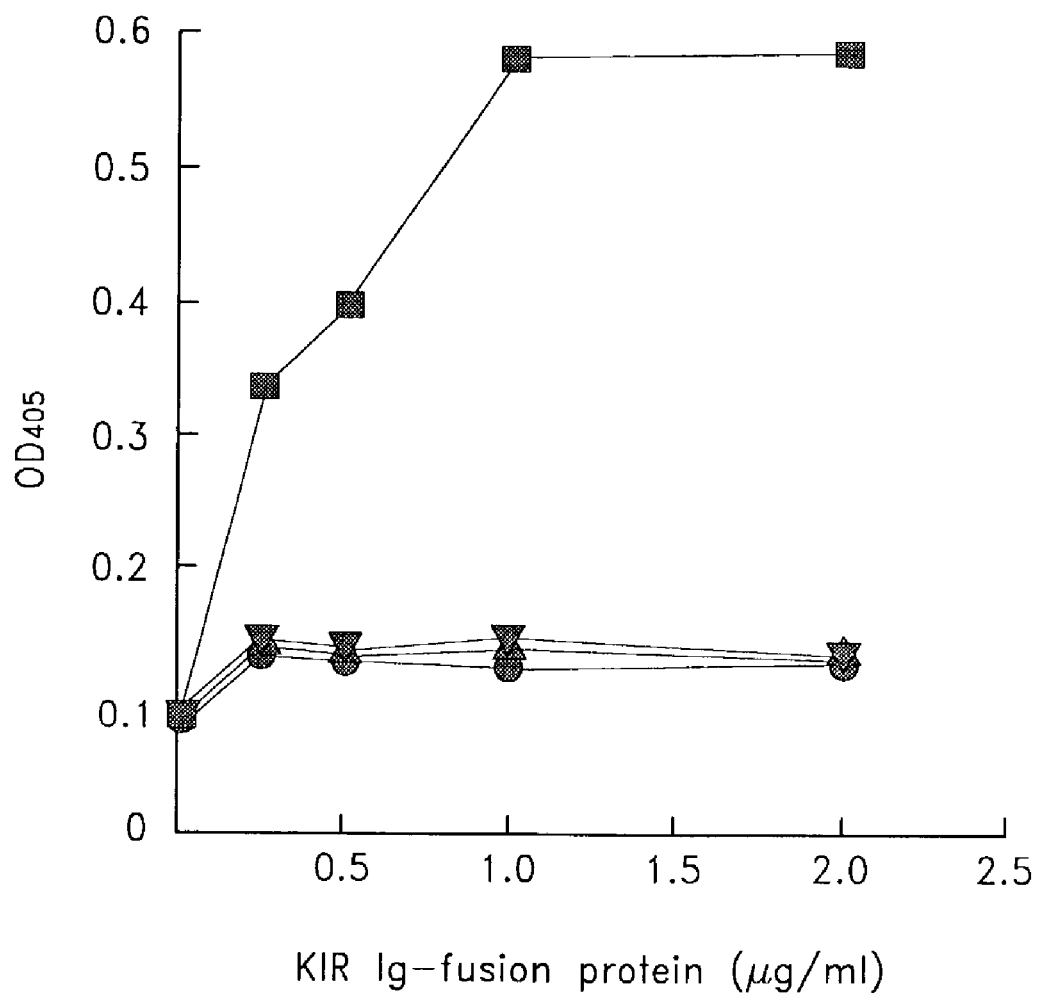
FIG. 4. The mAb 33 is specific for 2DL4 and stains NK cells. The KIR-Ig fusion proteins 2DL1 (●), 2DL2 (▲), 2DL3 (▼), 3DL1 (♦), and 2DL4 (■) were tested for reactivity with mAb 33 in an ELISA.

The mAbs against 2DL4 were generated to characterize the expression and signaling properties of 2DL4. One IgG (#33) and two IgMs (#36 and #64) were identified that reacted specifically with 2DL4 and not other KIR family members. In an ELISA, mAb 33 bound to 2DL4-Ig but not to KIR-Ig fusion proteins of 2DL1, 2DL2, 2DL3, and 3DL2 (FIG. 4). This mAb also did not bind KIR-Ig fusion proteins of 2DS2 and 2DS4. Similar results were obtained with the mAbs 36 and 64. These mAbs also reacted with cells transfected with 2DL4 but not 2DL5, a closely related KIR.

Figure 5:
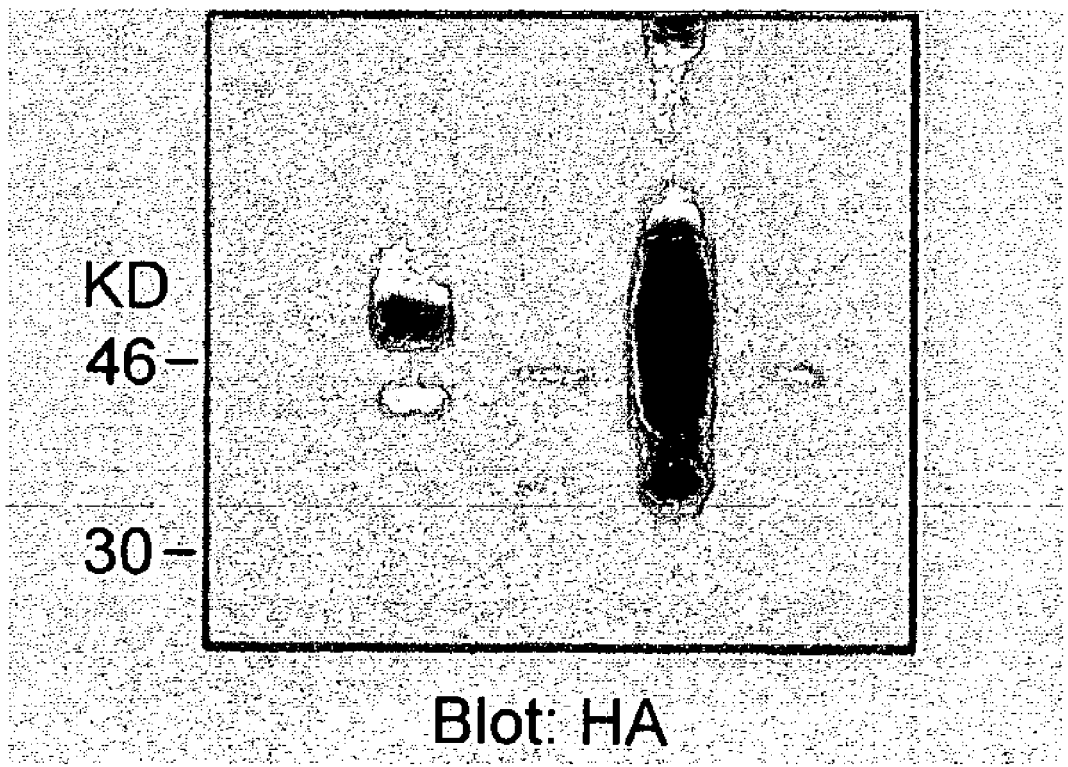
FIG. 5. The mAb 33 is specific for 2DL4 and stains NK cells. Total cell lysate (−) or immunoprecipitates (IP) using mAb 33 and DX27 from mock- or HA-2DL4-transfected 293T/17 cells were blotted with anti-HA.
Figure 6:
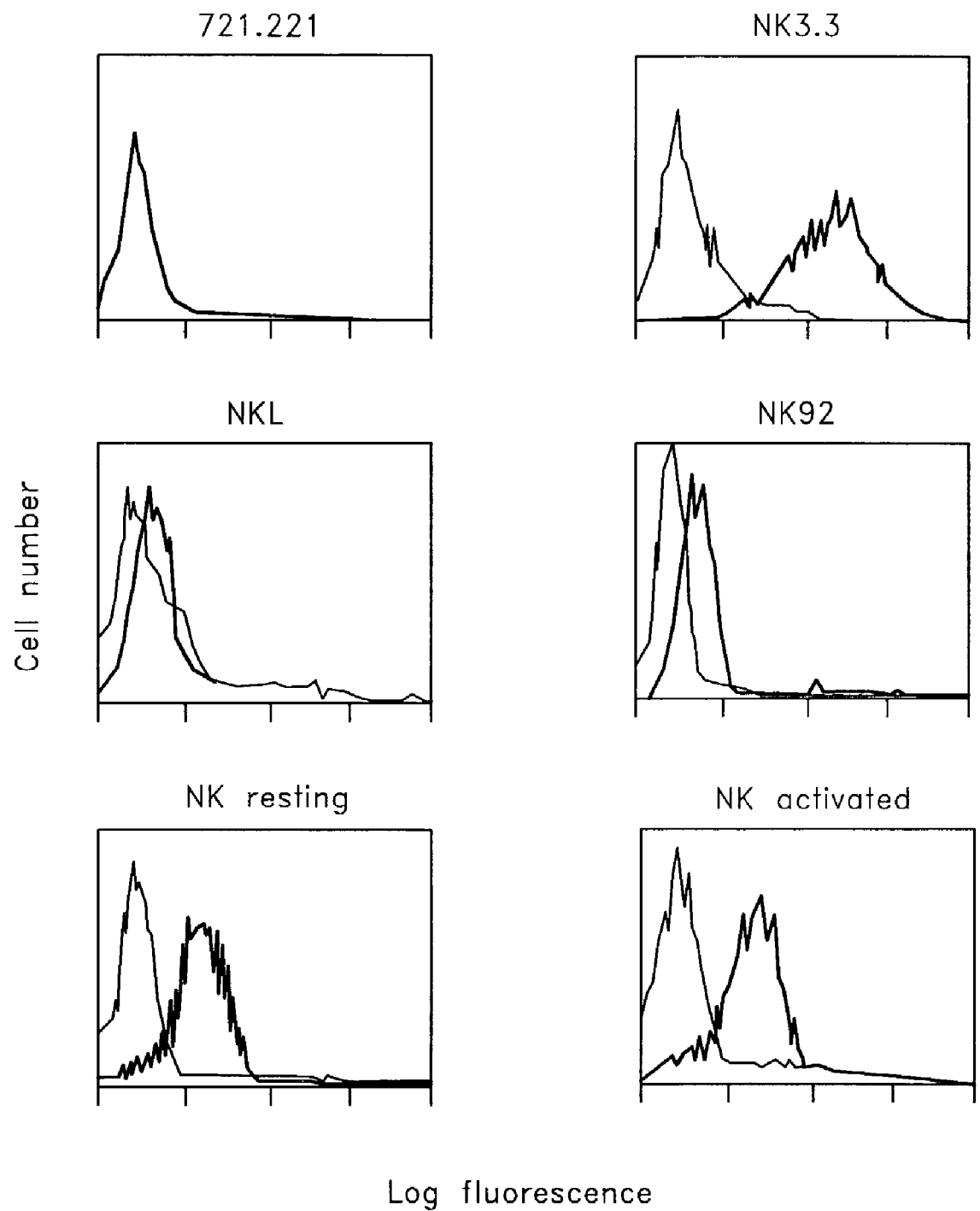
FIG. 6. The mAb 33 is specific for 2DL4 and stains NK cells. Surface 2DL4 expression of the indicated cell lines and of NK cells from a normal donor as detected with mAb 33. The thin lines indicate staining with control Abs.

Lysates of 293T/17 cells transfected with a cDNA encoding an epitope-tagged 2DL4 (HA-2DL4) were immunoprecipitated with mAb 33. Western blotting for the HA epitope revealed a broad 45- to 50-kDa band similar to that seen by blotting of the total cell lysate (FIG. 5). All three anti-2DL4 mAbs bound to the NK cell line NK3.3, but not to the B cell line 721.221 and the T cell line Jurkat as shown by flow cytometry (FIG. 6). The NK cell lines NKL and NK92 displayed low levels of cell surface 2DL4. NK cells isolated from peripheral blood of different donors varied from low (similar to that seen with NK92) to intermediate (as shown in FIG. 6) reactivity with the different anti-2DL4 mAbs.

Figure 7:
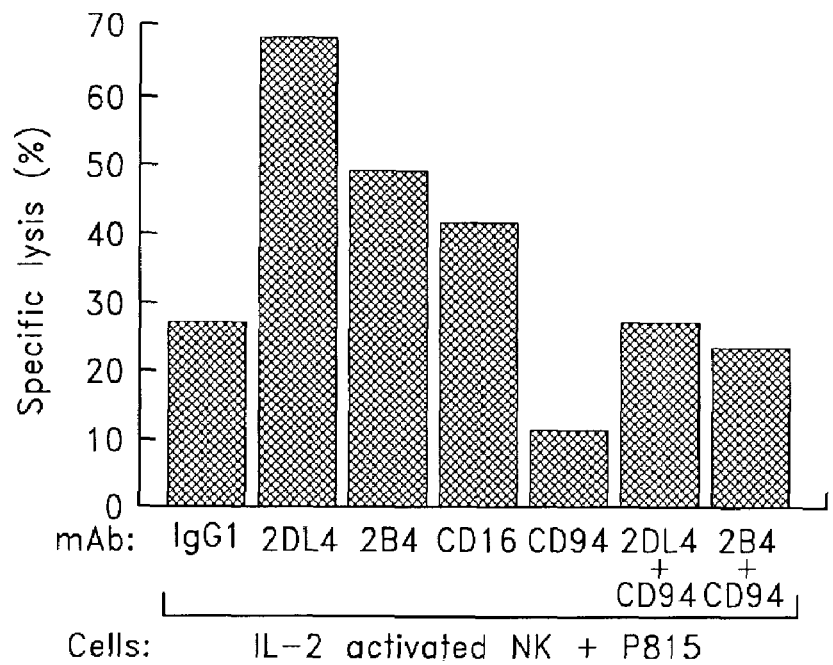
FIG. 7. Cross-linking 2DL4 induces cytotoxicity in IL-2 activated NK cells but not in resting NK cells. IL-2-activated NK cells were incubated with P815 cells (E:T ratio of 2) in the presence of the indicated mAbs (1 μg/ml). The ratio of lysis over that obtained with control Ig was 3.6±0.23 for 2DL4 (n=15), 3.3±0.59 for 2B4 (n=6), and 4.8±0.39 for CD16 (n=15).

The 2DL4-specific mAb 33 was used to test whether 2DL4 induces activation or inhibition of lysis. Lysis of the FcR-positive P815 cells by IL-2-activated NK cells in the presence of mAb 33 was comparable to that obtained with mAbs to the activation receptors 2B4 and CD16 (FIG. 7). Lysis of P815 cells induced by mAb 33 was also obtained with several NK cell clones and with the cell lines NK92, NKL, and NK3.3. We conclude that 2DL4 has properties of an activation receptor.

To test the outcome of 2DL4 coligation with an inhibitory receptor, NK cells that express mainly the CD94/NKG2A inhibitory receptor were selected among different donors (Valiante, N. M. et al. 1997 *Immunity* 7:739). Coligation of CD94/NKG2A inhibited the lysis induced by 2DL4, 2B4, and CD16 (FIG. 7). Thus, the activation signal delivered by 2DL4 in activated NK cells is typical of NK activation receptors that are sensitive to inhibition by ITIM-containing receptors.

Figure 8:
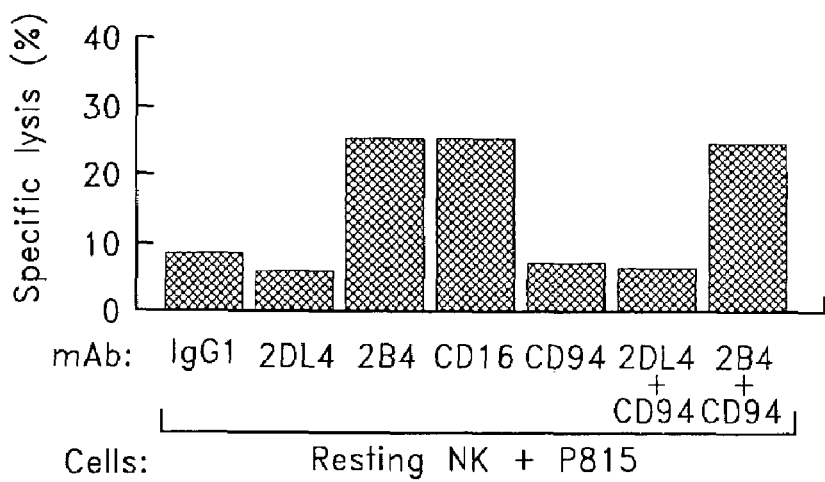
FIG. 8. Cross-linking 2DL4 induces cytotoxicity in IL-2 activated NK cells but not in resting NK cells. Cytotoxicity of resting NK cells against P815 cells (E:T ratio of 2) in the presence of the indicated mAbs. The ratio of lysis over that obtained with control Ig was 4.9±0.47 for CD16 (n=16), 3.1±0.11 for 2B4 (n=13), and 1.07±0.02 for 2DL4 (n=16).

Resting NK cells were incubated with P815 cells in the presence of mAbs for 2DL4, CD16, and 2B4 (FIG. 8). Enhancement of lysis by CD16 and by 2B4 was similar to that obtained with activated NK cells, except for the weaker lytic potential of freshly isolated NK cells. In contrast, 2DL4 did not enhance cytotoxic activity in resting NK cells. Thus, 2DL4 induction of killing was restricted to activated NK cells, distinguishing its activity from that of CD 16 and 2B4. Coligation of 2B4 or CD 16 with CD94 did not decrease the level of lysis (FIG. 8), even though resting NK populations were chosen that yielded activated NK cells in which CD94 was inhibitory. Time course (6-72 h) and titration studies with 0.1-16 µg/ml of the Abs against 2DL4, 2B4, and CD16 were done to ensure that the unique induction of IFN-gamma but not cytotoxicity upon 2DL4 activation was not a function of the intensity of mAb triggering.

The Transmembrane Region of 2DL4 is Necessary for the Activation Signal.

Figure 9:
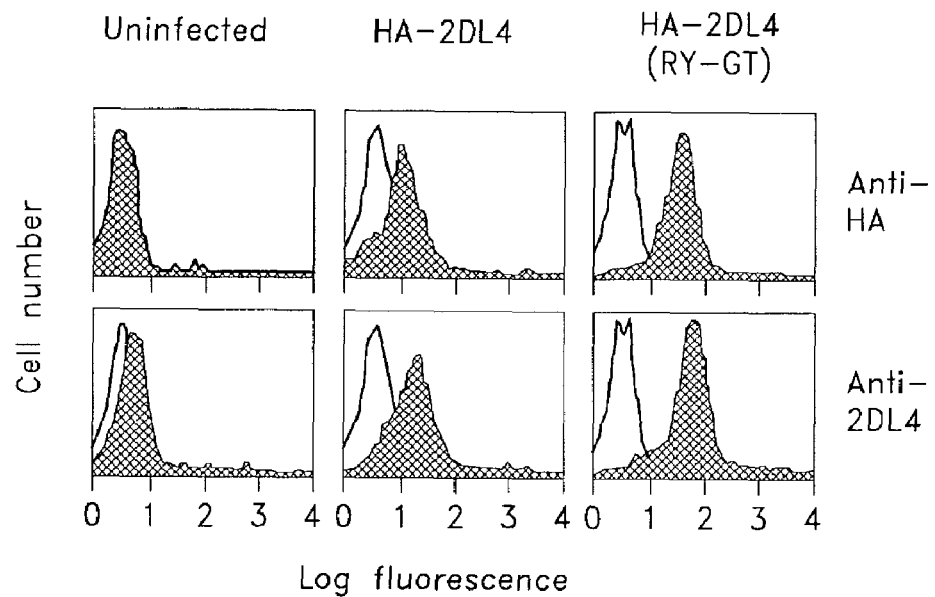
FIG. 9. An intact transmembrane region of 2DL4 is required for the activation signal. Recombinant vaccinia viruses encoding HA-2DL4 or (RY-GT) mutant of HA-2DL4 were used to infect IL-2-activated NK cells. Flow cytometry analysis after infection using either anti-HA mAb or anti-2DL4 mAbs.
Figure 10:
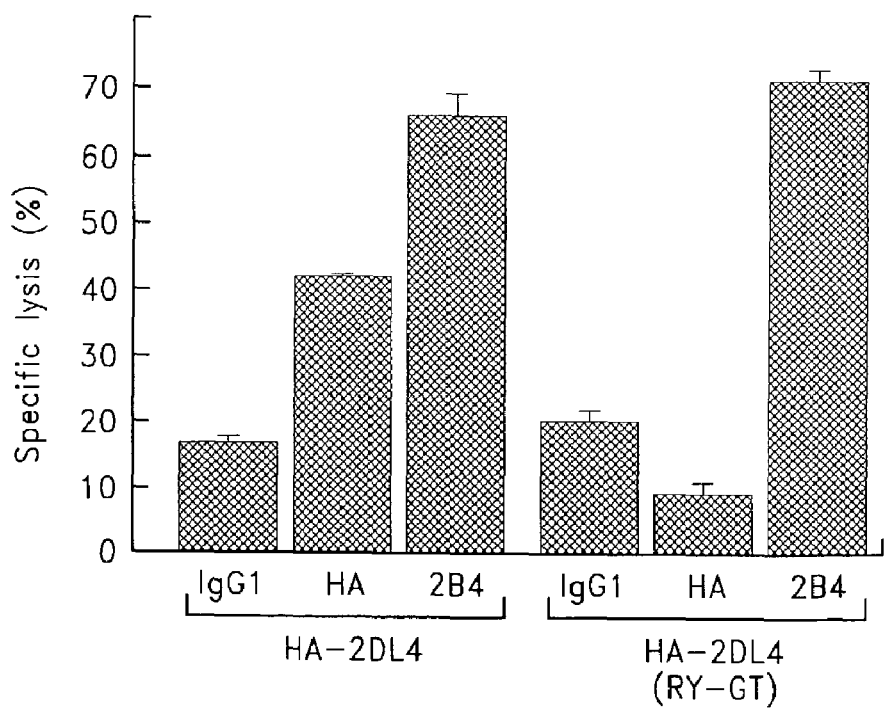
FIG. 10. An intact transmembrane region of 2DL4 is required for the activation signal. Recombinant vaccinia viruses encoding HA-2DL4 or (RY-GT) mutant of HA-2DL4 were used to infect IL-2-activated NK cells. Infected cells were used in a lysis assay with P815 cells (E:T ratio of 2) in the presence of mAbs as indicated. Fold activation: HA-2DL4/control Ig=2.9±0.18 (n=4); RY-GT mutant/control Ig=0.56±0.03 (n=4).

Recombinant vaccinia viruses encoding 2DL4 and a mutated 2DL4 in which the amino acids arginine-tyrosine in the transmembrane region were replaced by the glycine-threonine (mutant RY-GT) conserved in all other KIR receptors were generated. HA-2DL4 was used to distinguish recombinant from endogenous 2DL4. Homogenous surface expression of these receptors was obtained by infection of NK cell populations (FIG. 9). Ligation of wild-type HA-2DL4 receptor by anti-HA mAb resulted in activation of lysis of P815 cells (FIG. 10). In contrast, ligation of the RY-GT mutant did not result in activation despite higher expression of mutant RY-GT than wild-type HA-2DL4 and even though P815 lysis was induced by ligation of 2B4 in the same infected cells. The small reduction in lysis of P815 cells as compared to control Abs may be a function of the inhibitory effect mediated by the ITIM in the cytoplasmic tail. Mutation of the tyrosine in the ITIM to a phenylalanine did not diminish the ability of 2DL4 to activate lysis. We conclude that 2DL4-mediated activation requires an intact transmembrane domain but no ITIM. The unique arginine-tyrosine motif is conserved in the transmembrane region of 2DL4 in humans, chimpanzees, and rhesus monkeys (Khakoo, S. I. et al. 2000 Immunity 12:687; Hershberger, K. L. et al. 2001 J Immunol 166:4380). It is likely that the arginine in the transmembrane domain mediates association with a partner chain responsible for the activation signal, as seen with other NK-activating receptors that associate with either FcγR, DAP12, or DAP10 (Lanier, L. L. 2001 Nature Immunol 2:23). Transfection experiments in the Ba/F3 and 293T cell lines have also indicated that 2DL4 does not pair with FcRγ, DAP12, or DAP10 chains. Studies are anticipated to identify the putative partner chain of 2DL4.

2DL4 Induces Strong IFN-gamma Production by Resting NK Cells.

Figure 12:
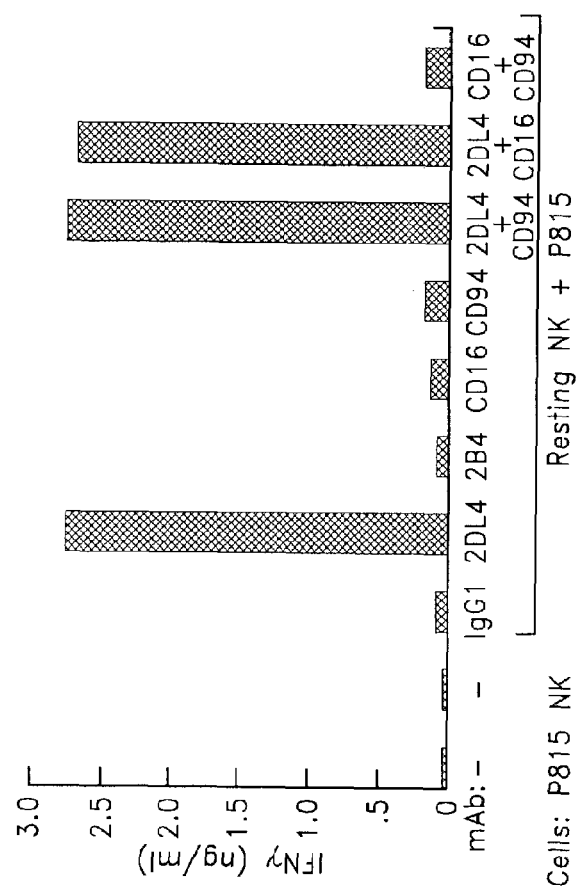
FIG. 12. 2DL4 induces IFN-gamma production in resting NK cells. IFN-gamma produced by resting NK cells incubated with P815 cells in the presence of the indicated mAbs. Increase in IFN-gamma release over control IgG was: 57±5.1 for 2DL4 (n=18), 2.1±0.15 for 2B4 (n=17), and 4.2±0.5 for CD16 (n=18).
Figure 11:
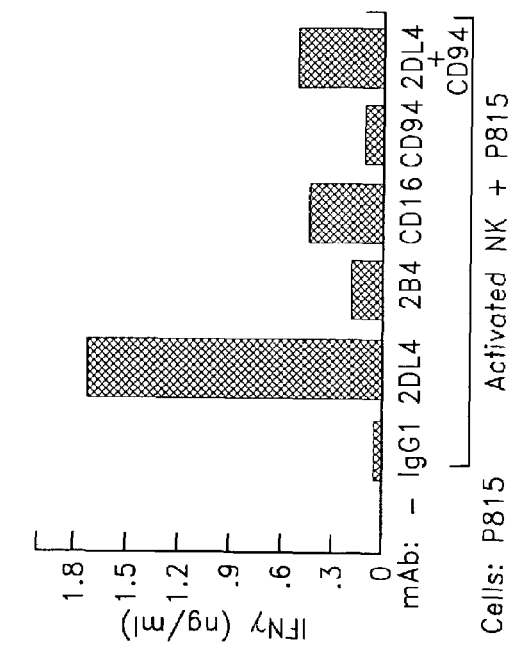
FIG. 11. 2DL4 induces IFN-gamma production in resting NK cells. IFN-gamma produced by IL-2-activated NK cells incubated with P815 cells for 20 h in the presence of receptor-specific mAbs (1 µg/ml). Increase in IFN-gamma release over that induced by control IgG was: 35.4 for 2DL4, 1.55 for 2B4, and 20.15 for CD16 (n=2).

IFN-gamma secretion in both activated and resting NK cells was measured after coculture with P815 cells in the presence of mAbs to NK receptors. In activated NK cells, the ability of 2DL4 to induce IFN-gamma was greater than that of the activation receptors CD16 and 2B4 (FIG. 11). As seen in cytotoxicity assays (FIG. 7), coligation of 2DL4 with CD94 resulted in inhibition of IFN-gamma production (FIG. 11). Activation of IFN-gamma production by 2DL4 cross-linking was even more striking in resting NK cells (FIG. 12). By comparison, ligation of 2B4 and CD16 induced a much smaller response. Coligation of 2DL4 with CD16 had no additional effect on IFN-gamma secretion (FIG. 12). Therefore, in resting NK cells, 2DL4 is unique in its ability to induce efficient IFN-gamma production in the absence of any discernible lytic function. Intracellular staining of IFN-gamma in both activated and resting NK cells stimulated with 2DL4 revealed that expression occurred in the bulk of the NK cell population in contrast to the selective expression of IFN-gamma by $CD56^{bright}$ NK cells in response to IL-12 (Cooper, M. A. et al. 2001 Blood 97:3146).

Co-cross-linking of CD94 with 2DL4 on activated NK cells inhibited lysis and IFN-gamma production (FIGS. 7 and 11). In contrast, similar co-cross-linking on resting NK cells did not inhibit IFN-gamma secretion induced by 2DL4 (FIG. 12) or lysis induced by 2B4 (FIG. 8). Expansion of NK cells from this resting NK population yielded cells with inhibitory CD94. The lack of 2DL4 sensitivity to CD94-mediated inhibition in resting cells could be due to different repertoires of CD94/NKG2 on resting vs. activated NK cells. Alternatively, the ITIM-based inhibitory pathway may not function in resting NK cells. In any case, it is significant that activation through 2DL4 in resting NK cells is not inhibited by the receptor for HLA-E.

Figure 13:
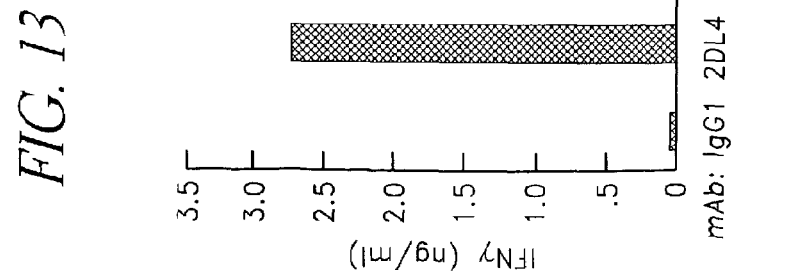
FIG. 13. 2DL4 induces IFN-gamma production in resting NK cells. IFN-gamma production by the same resting NK cells as in FIG. 12 incubated with either isotype-matched control mAb or mAb against CD16 or 2DL4 (33) in the absence of secondary Ab. On the right, resting NK cells from a different donor were incubated with isotype-matched controls and with Abs 33 (IgG), 36 (IgM), and 64 (IgM) for 20 h. Enhancement of IFN-gamma production over control Ig was: 66±5.9 for 33 (n=16), 150±37 for 36 (n=5), and 92±22 for 64 (n=5).

Robust IFN-gamma production was obtained by incubation with the IgG1 33 or either one of the two IgM mAbs in the absence of further cross-linking (FIG. 13). The use of the two IgM mAbs, 36 and 64, excluded a role of FcγR in the activation by 2DL4. Therefore, the signal transduced by 2DL4 alone induces IFN-gamma production by resting NK cells in the absence of cytokines or signals from other receptors. In contrast, engaging the receptors CD16 and 2B4 with soluble mAbs is not sufficient, and additional accessory interactions are needed to trigger IFN-gamma release (Watzl, C. et al. 2000 J Immunol 165:3545; Valiante, N. M. and G. Trinchieri 1993 J Exp Med 178:1397).

Figure 14:
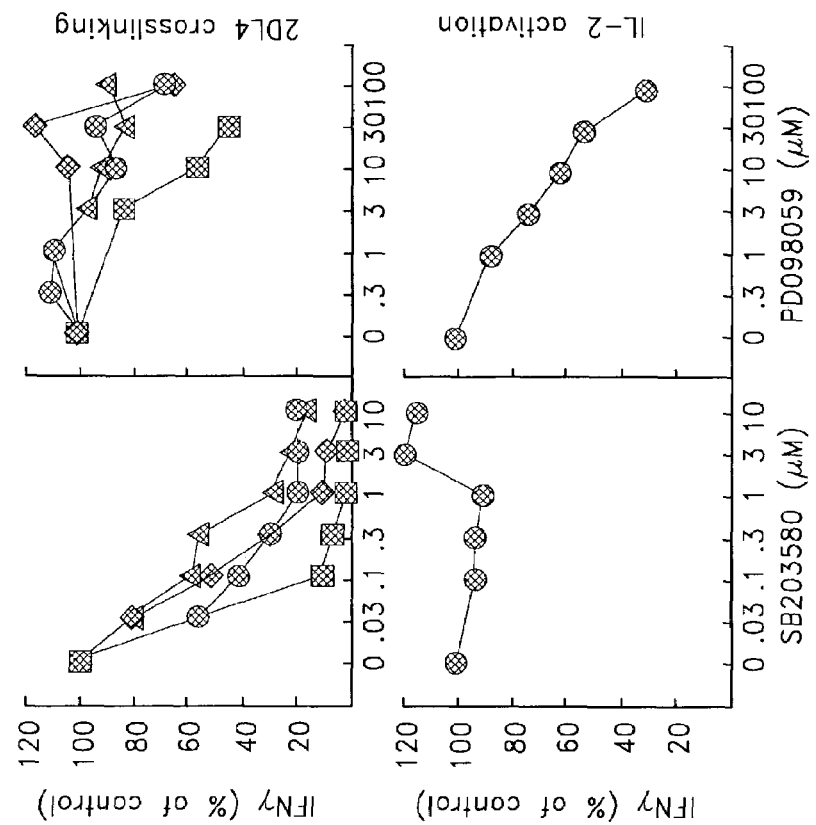
FIG. 14. 2DL4 induces IFN-gamma production in resting NK cells. IFN-gamma secretion by resting NK cells treated with MEK1 and p38 MAPK inhibitors. Top, Cells were incubated with SB203580 or PD098059 for 1 h at 37° C. before activation with anti-2DL4 mAb for 20 h in the continuing presence of inhibitor. The four curves represent resting NK cells from four different donors. The IFN-gamma release in the absence of inhibitor with resting NK cells from the different donors ranged between 660 and 1490 pg/ml. Bottom, IFN-gamma release by resting NK cells incubated with inhibitors for 2 h before activation with rIL-2 (5 U/ml) for 20 h in the continuing presence of inhibitor.

The IFN-gamma secretion by NK cells induced by IL-2 depends on an ERK mitogen-activated protein kinase pathway (Yu, T. K. et al. 2000 J Immunol 164:6244). The ERK-dependent IFN-gamma secretion was also observed upon cross-linking of CD16 or $\beta_1$ integrin on activated NK cells or by mixing NK cells with the sensitive target cell line K562 (Trotta, R. et al. 1998 J Immunol 161:6648; Mainiero, F. et al. 2000 Immunity 12:7). Inhibitors of MEK1 (PD98059) and of p38 MAPK (SB203580) were added to resting NK cells during stimulation with anti-2DL4 mAbs to test whether 2DL4-induced production of IFN-gamma required MAPK (FIG. 14, top). Complete inhibition occurred at 1 μM of the p38 inhibitor SB203580. The ERK pathway inhibitor, PD98059, had only a partial inhibitory effect. In contrast, the IL-2-mediated induction of IFN-gamma production was severely inhibited by 50 μM PD98059 and unaffected by SB203580 (FIG. 14, bottom), as previously reported (Yu, T. K. et al. 2000 J Immunol 164:6244). Thus, the p38 MAPK-dependent 2DL4 signal for IFN-gamma secretion is different from signals delivered to activated NK cells by CD16 and $\beta_1$ integrin and to resting NK cells by the IL-2R, which are all sensitive to an ERK MAPK inhibitor. Further biochemical analysis of the 2DL4 signaling pathway is anticipated. Polarization of cytotoxic granules in NK cells, leading to target cell killing, is also ERK-dependent (Perussia, B. 2000 Nature Immunol 1:372). The use of a p38 rather than an ERK pathway for activation of resting NK cells by 2DL4 may be designed to avoid cytotoxicity while maintaining the IFN-gamma response. In this regard, IFN-gamma induction by 2DL4 is similar to IFN-gamma production by Th1 cells and to IFN-gamma gene transcription in T cells stimulated by IL-12 and IL-18 that are also regulated by p38 (Rincon, M. et al. 1998 EMBO J 17:2817; Yang, J. et al. 2001 Nature Immunol 2:157).

To fully understand the physiological relevance of 2DL4-mediated IFN-gamma production, the ligands that recognize this receptor need to be identified. One ligand that interacts with 2DL4 is HLA-G, because 2DL4 binds to cells expressing HLA-G (Cantoni, C. et al. 1998 Eur J Immunol 28:1980; Rajagopalan, S. and E. O. Long. 1999 [published erratum appears in J Exp Med 2000 191:2027] J Exp Med 189:1093; Ponte, M. et al. 1999 PNAS USA 96:5674). HLA-G is expressed by fetal trophoblast cells that invade maternal decidua where they encounter NK cells during early pregnancy (Loke, Y. W. and A. King. 1997 Mol Med Today 3:153). Uterine NK cells are a major source of IFN-gamma in pregnant mice, where IFN-gamma has an important role in vascularization at the implantation site (Ashkar, A. A. et al. 2000 J Exp Med 192:259.). We have observed enhanced IFN-gamma production by resting NK cells in the presence of HLA-G-expressing cells. A role is anticipated for 2DL4 in stimulating IFN-gamma production during pregnancy.

This disclosure has identified 2DL4 as a receptor with the unique and autonomous ability to induce rapid IFN-gamma secretion but not cytotoxicity by resting NK cells in the absence of cytokines. Signals that can activate resting NK cells have physiological relevance to the in vivo induction of NK responses. Furthermore, we show that resting NK cells behave differently than activated NK cells in terms of the outcomes of receptor activation. This is noteworthy since most studies on NK receptor function are conducted using IL-2-activated NK cell populations or clones. The polarized response of resting NK cells to signals received from 2DL4 vs. other activation receptors is analogous to the distinct NK responses induced by different cytokines and reveals another facet in the complex regulation of these effector cells.

Definitions

The term "isolated" requires that a material be removed from its original environment (e.g., the natural environment if it is naturally occurring). For example, a naturally occurring polynucleotide or polypeptide present in a living cell is not isolated, but the same polynucleotide or polypeptide, separated from some or all of the coexisting materials in the natural system, is isolated.

The term "purified" does not require absolute purity; rather it is intended as a relative definition, with reference to the purity of the material in its natural state. Purification of natural material to at least one order of magnitude, preferably two or three magnitudes, and more preferably four or five orders of magnitude is expressly contemplated.

The term "enriched" means that the concentration of the material is at least about 2, 5, 10, 100, or 1000 times its natural concentration (for example), advantageously 0.01% by weight. Enriched preparations of about 0.5%, 1%, 5%, 10%, and 20% by weight are also contemplated.

The KIR2DL4 Receptor Gene

The KIR2DL4 receptor is encoded by the KIR2DL4 cDNA. The nucleotide sequence of the cDNA can be found in *Tissue Antigens* (Oct. 1996) "NK cell receptor gene of the KIR family with two IG domains by highest homology to KIR receptors with three IG domains," 48 (4 pt 1):285-94 by Selvakumar, Steffens, and Dupont.

The KIR2DL4 Receptor Protein

Figure 2:
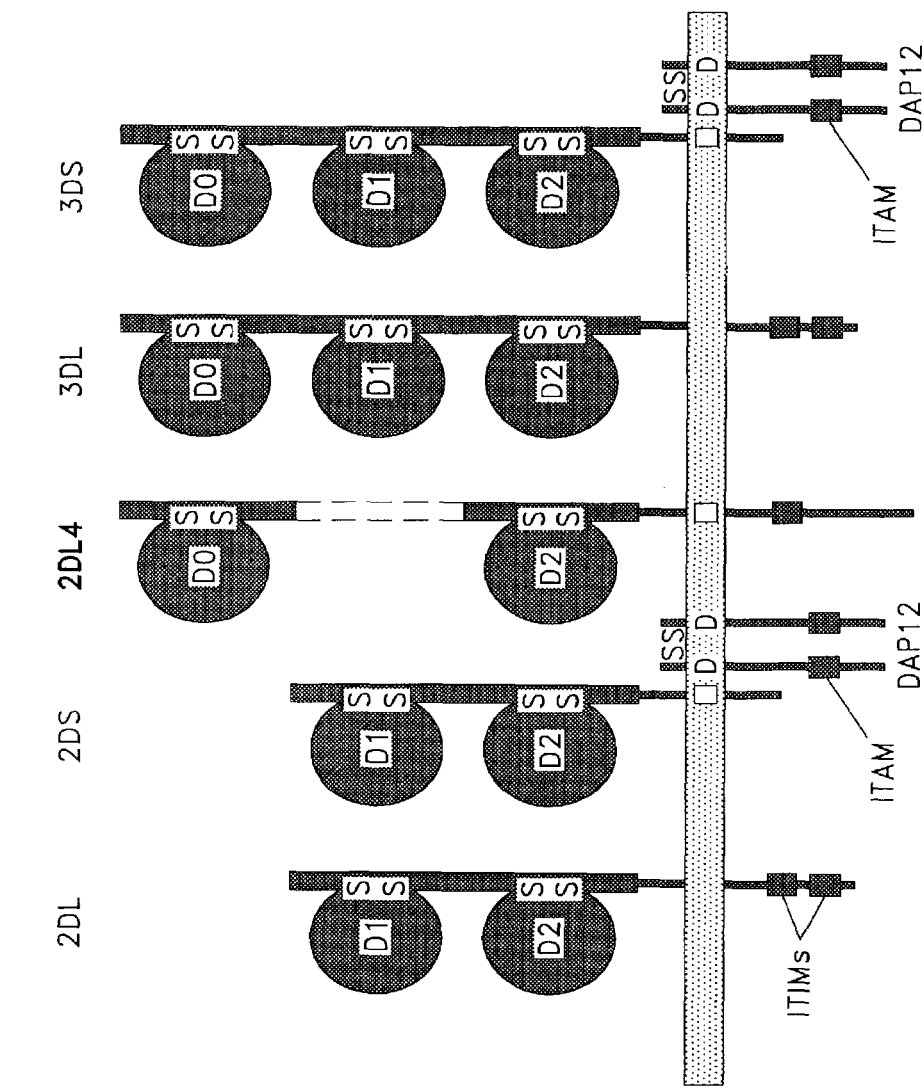
FIG. 2. KIR family receptor proteins. KIR2DL4 is a structurally divergent member of the KIR family with the D0 domain present in the 3D KIRs fused to the D2 domain. Additionally, unlike the other inhibitory 2D and 3D KIR that have 2 ITIM motifs, KIR2DL4 has a single ITIM. KIR2DL4 also has a charged residue in the transmembrane domain like the 2DS and 3DS receptors that are activating by virtue of their association with the ITAM-containing DAP12 adaptor protein. Thus, KIR2DL4 has both an activating and inhibitory potential. KIR2DL4 also differs from the rest of the KIR family because it is the only KIR expressed on all human NK cells.
Figure 3:
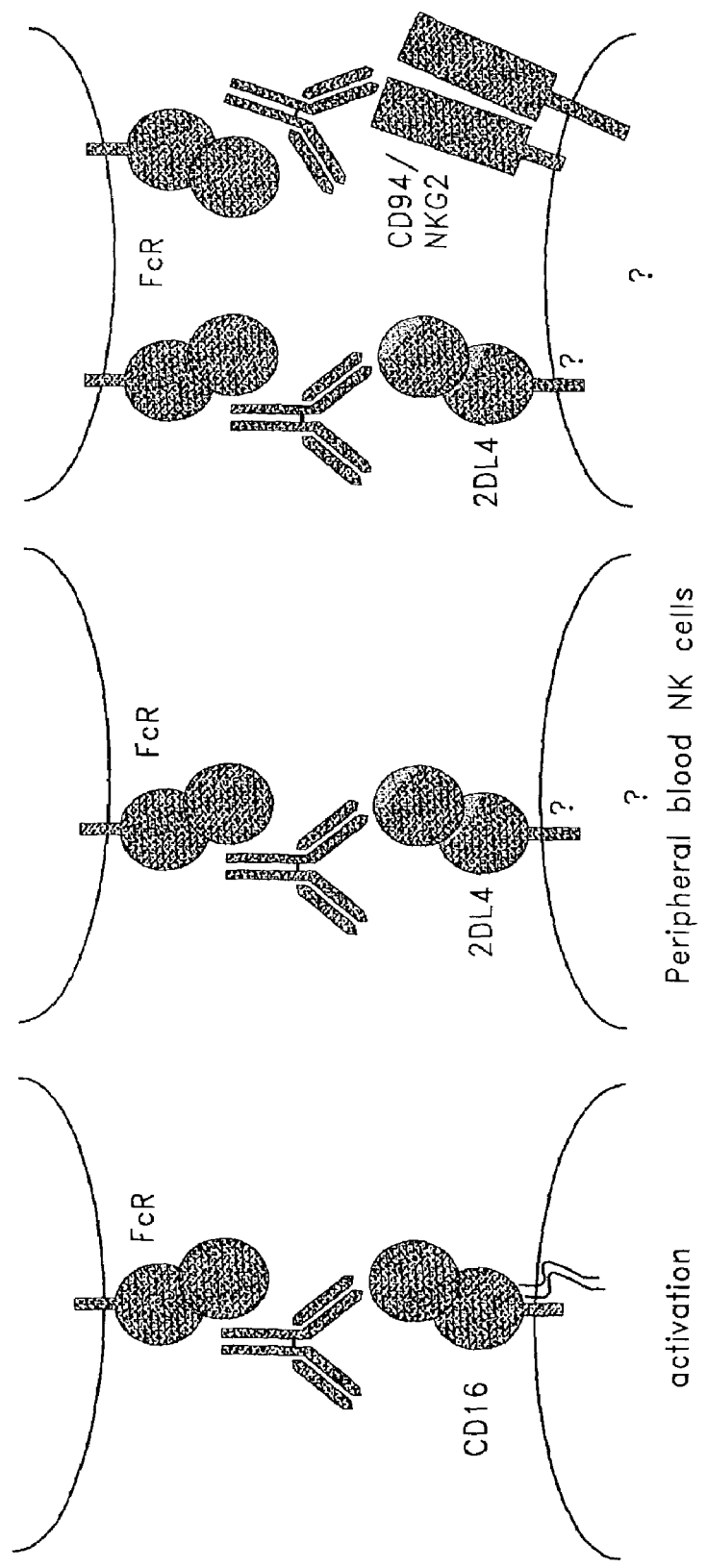
FIG. 3. Cross-linking of 2DL4 on peripheral NK cells. A redirected ADCC assay tests effects of receptor cross-linking on NK cell activation. According to the assay, target cells, such as FcR$^+$P815 cells, are mixed with NK cells in the presence of mAb. If the receptor is activating, the mAb will induce cytolytic activity, presumably by engaging the target cell by the Fc portion, and the receptor by the Fab portion, as in the case of an activating receptor CD16. This assay permits determination of the outcome of KIP2DL4 cross-linking by a specific mAb and KIR2DL4 co-cross-linking with the CD94/NKG2 receptor that is an inhibitory receptor when CD94 is paired with NKG2.

The KIR2DL4 receptor protein predicted by the cDNA is a member of the KIR (killer cell immunoglobulin like receptors) family receptor proteins. Referring to FIGS. 1, 2, can 3, the KIR family is a group of glycoproteins expressed in natural killer cells and some T cells. The KIR family is estimated to include about 11 genes. The KIR family is subdivided into two subfamilies based on structure: KIR2D and KIR3D, with further subdivision into forms with short and long cytoplasmic tails. Typically, KIR with a long cytoplasmic tail (L) delivers an inhibitory signal, whereas KIR with a short cytoplasmic tail (S) can activate NK or T cell responses. The first and second Ig domains in KIR2D are closely related in amino acid sequence to the second and third Ig domains in KIR3D. These two related Ig domains are called D1 and D2, respectively. D0 is the first Ig domain in KIR3D. Most of the long cytoplasmic tails carry two immunoreceptor tyrosine-based inhibition motifs (ITIM). The short cytoplasmic tails are truncated before the first ITIM and are connected to a transmembrane region which includes a lysine residue. Specifically KIR2DL4 is characterized by having an unusual D0-D2 Ig configuration, a transmembrane region containing an arginine residue, and a long cytoplasmic tail of 114 amino acids with the first ITIM only.

While the KIR2DL4 receptor can be chemically synthesized (e.g., see Creighton, 1983, Proteins: Structures and Molecular Principles, W.H. Freeman & Co., N.Y.), peptides and polypeptides derived from the KIR2DL4 receptor and the full length KIR2DL4 itself may advantageously be produced by recombinant DNA technology using techniques well known in the art for expressing nucleic acid containing KIR2DL4 gene sequences and/or coding sequences. Such methods can be used to construct expression vectors containing the KIR2DL4 nucleotide sequences and appropriate transcriptional and translational control signals. These methods include, for example, in vitro recombinant DNA techniques, synthetic techniques, and in vivo genetic recombination. See, for example, the techniques described in Sambrook et al. 1989 *Molecular Cloning, A Laboratory Manual*, Cold Springs Harbor Press, N.Y.; and Ausubel et al. 1989 *Current Protocols in Molecular Biology*, Green Publishing Associates and Wiley Interscience, N.Y.

A variety of host-expression vector systems may be utilized to express KIR2DL4 nucleotide sequences. The expression systems encompass engineered host cells that express KIR2DL4 or functional equivalents in situ, i.e., anchored in the cell membrane. Such engineered host cells may be used in situations where it is important not only to retain the structural and functional characteristics of KIR2DL4, but to assess biological activity, e.g., in drug screening assays.

The expression systems that may be used for purposes of the invention include but are not limited to microorganisms such as bacteria (e.g., *E. coli, B. subtilis*) transformed with recombinant bacteriophage DNA, plasmid DNA or cosmid DNA expression vectors containing KIR2DL4 nucleotide sequences; yeast (e.g., Saccharomyces, Pichia) transformed with recombinant yeast expression vectors containing KIR2DL4 nucleotide sequences; insect cell systems (e.g., SF9) infected with recombinant virus expression vectors (e.g., baculovirus) containing the KIR2DL4 sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing KIR2DL4 nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the KIR2DL4 gene product being expressed. For example, vectors which direct the expression of high levels of fusion protein products that are readily purified may be desirable. Such vectors include, but are not limited to, the *E. coli* expression vector pUR278 (Ruther et al. 1983 *EMBO J* 2:1791), in which the KIR2DL4 coding sequence may be ligated individually into the vector in frame with the lacZ coding region so that a fusion protein is produced; pIN vectors (Inouye & Inouye 1985 *Nucleic Acids Res* 13:3101-3109; Van Heeke & Schuster 1989 *J Biol Chem* 264:5503-5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhidrosis virus (AcNPV) is used as a vector to express foreign genes. The virus grows in *Spodoptera frugiperda* cells. The KIR2DL4 gene coding sequence may be cloned into nonessential regions (for example the polyhedrin gene) of the virus and placed under control of an AcNPV promoter (for example the polyhedrin promoter). Successful insertion of KIR2DL4 gene coding sequence will result in inactivation of the polyhedrin gene and production of non-occluded recombinant virus, (i.e., virus lacking the proteinaceous coat coded for by the polyhedrin gene). These recombinant viruses are then used to infect *Spodoptera frugiperda* cells in which the inserted gene is expressed (e.g., see Smith et al. 1983 *J Virol* 46:584; Smith, U.S. Pat. No. 4,215,051).

In mammalian host cells, a number of viral-based expression systems may be utilized. In cases where a vaccinia virus is used as an expression vector, the KIR2DL4 nucleotide sequence of interest may be ligated to a promoter and/or leader sequence. This chimeric gene may then be inserted in the vaccinia virus genome by in vitro or in vivo recombination. Insertion in a non-essential region of the viral genome will result in a recombinant virus that is viable and capable of expressing the KIR2DL4 gene product in infected hosts. Specific initiation signals may also be required for efficient translation of inserted KIR2DL4 nucleotide sequences. These signals include the ATG initiation codon and adjacent sequences. In cases where an entire KIR2DL4 gene or cDNA, including its own initiation codon and adjacent sequences, is inserted into the appropriate expression vector, no additional translational control signals may be needed. However, in cases where only a portion of the KIR2DL4 coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See, Bittner et al. 1987 *Methods in Enzymol* 153:516-544).

In addition, a host cell strain may be chosen, which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells, which possess the cellular machinery for proper processing of the primary transcript, glycosylation, and phosphorylation of the gene product, may be used. Such mammalian host cells include, but are not limited to, CHO, VERO, BHK, HeLa, COS, MDCK, 293, 3T3, W138.

For long-term, high-yield production of recombinant proteins, stable expression is preferred. For example, cell lines, which stably express the KIR2DL4 sequences described above, may be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines, which express the KIR2DL4 gene product. Such engineered cell lines may be particularly useful in screening and evaluation of compounds that affect the biological activity of the KIR2DL4 gene product.

A number of selection systems may be used, including but not limited to the herpes simplex virus thymidine kinase (Wigler et al. 1977 *Cell* 11:223), hypoxanthine-guanine phosphoribosyltransferase (Szybalska & Szybalski 1962 *PNAS USA* 48:2026), and adenine phosphoribosyltransferase (Lowy et al. 1980 *Cell* 22:817) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler et al. 1980 *PNAS USA* 77:3567; O'Hare et al. 1981 *PNAS USA* 78:1527); gpt, which confers resistance to mycophenolic acid (Mulligan & Berg 1981 *PNAS USA* 78:2072); neo, which confers resistance to the aminoglycoside G-418 (Colberre-Garapin et al. 1981 *J Mol Biol* 150:1); and hygro, which confers resistance to hygromycin (Santerre et al. 1984 *Gene* 30:147).

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht et al. 1991 *PNAS USA* 88:8972-8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto Ni$^{2+}$ nitriloacetic acid-agarose columns and histidine-tagged proteins are selectively eluted with imidazole-containing buffers.

Antibodies to KIR2DL4 Receptor

Antibodies that specifically recognize one or more epitopes of KIR2DL4 receptor, or epitopes of conserved mutants of KIR2DL4 receptor or peptide fragments of KIR2DL4 receptor and that modulate, i.e., stimulate or inhibit, production of interferon gamma are encompassed by the invention. Such antibodies include but are not limited to polyclonal antibodies, monoclonal antibodies (mAbs), humanized or chimeric antibodies, single chain antibodies, Fab fragments, F(ab')2 fragments, fragments produced by a Fab expression library, and epitope-binding fragments of any of the above.

For the production of antibodies, various host animals may be immunized by injection with KIR2DL4, a KIR2DL4 peptide (e.g., one corresponding to a functional domain), truncated KIR2DL4 proteins, polypeptides, or peptides, functional equivalents of KIR2DL4 or mutants of KIR2DL4. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Polyclonal antibodies are heterogeneous populations of antibody molecules derived from the sera of the immunized animals.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (1975, Nature 256:495-497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026-2030), and the EBV-hybridoma technique (Cole et al., 1985, Monoclonal Antibodies And Cancer Therapy, Alan R. Liss, Inc., pp. 77-96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of chimeric antibodies (Morrison et al., 1984, Proc. Natl. Acad. Sci., 81:6851-6855; Neuberger et al., 1984, Nature, 312:604-608; Takeda et al., 1985, Nature, 314:452-454) by splicing the genes from a mouse antibody molecule of appropriate antigen specificity together with genes from a human antibody molecule of appropriate biological activity can be used. Humanized antibodies produced by conventional complementarity determining regions (CDR) grafting methods are also within the scope of this invention.

Alternatively, techniques described for the production of single chain antibodies (U.S. Pat. No. 4,946,778; Bird, 1988, Science 242:423-426; Huston et al., 1988, Proc. Natl. Acad. Sci. USA 85:5879-5883; and Ward et al., 1989, Nature 334: 544-546) can be adapted to produce single chain antibodies against KIR2DL4 gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the F(ab')2 fragments which can be produced by pepsin digestion of the antibody molecule and the Fab fragments which can be generated by reducing the disulfide bridges of the F(ab')2 fragments. Alternatively, Fab expression libraries may be constructed (Huse et al., 1989, Science, 246:1275-1281) to allow rapid and easy identification of monoclonal Fab fragments with the desired specificity.

Screening Assays for Compounds that Modulate KIR2DL4 Expression or Activity

The following assays are designed to identify compounds that interact with (e.g., bind to) KIR2DL4, compounds that interact with (e.g., bind to) intracellular proteins that interact with KIR2DL4, compounds that modulate the interaction of KIR2DL4 with transmembrane or intracellular proteins involved in KIR2DL4-mediated signal transduction, and to compounds which modulate the activity of KIR2DL4 gene (i.e., modulate the level of KIR2DL4 gene expression) or modulate the level of KIR2DL4. Assays may additionally be utilized which identify compounds which bind to KIR2DL4 gene regulatory sequences (e.g., promoter sequences) and which may modulate KIR2DL4 gene expression. See, e.g., Platt, K. A. 1994 *J Biol Chem* 269:28558-28562.

The compounds which may be screened in accordance with the invention include, but are not limited to peptides, antibodies and fragments thereof, and other organic compounds (e.g., peptidomimetics) that bind to the extracellular domain of the KIR2DL4 and either mimic the activity triggered by the natural ligand (i.e., agonists) or inhibit the activity triggered by the natural ligand (i.e., antagonists); as well as peptides, antibodies or fragments thereof, and other organic compounds that mimic the extracellular domain of the KIR2DL4 (or a portion thereof) and bind to and "neutralize" natural ligand.

Such compounds may include, but are not limited to, peptides such as, for example, soluble peptides, including but not limited to members of random peptide libraries (see, e.g., Lam, K. S. et al. 1991 *Nature* 354:82-84; Houghten, R. et al. 1991 *Nature* 354:84-86), and combinatorial chemistry-derived molecular library made of D- and/or L-configuration amino acids, phosphopeptides (including, but not limited to, members of random or partially degenerate, directed phosphopeptide libraries (see, e.g., Songyang, Z. et al. 1993 *Cell* 72:767-778), antibodies (including, but not limited to, polyclonal, monoclonal, humanized, chimeric or single chain antibodies, and Fab, F(ab')$_2$ and Fab expression library fragments, and epitope-binding fragments thereof), and small organic or inorganic molecules.

Other compounds which can be screened in accordance with the invention include but are not limited to small organic molecules that affect the expression of the KIR2DL4 gene or some other gene involved in the KIR2DL4 signal transduction pathway (e.g., by interacting with the regulatory region or transcription factors involved in gene expression); or such compounds that affect the activity of KIR2DL4 (e.g., by inhibiting or enhancing the enzymatic activity of the cytoplasmic domain) or the activity of some other intracellular factor involved in the KIR2DL4 signal transduction pathway.

Computer modeling and searching technologies permit identification of compounds, or the improvement of already identified compounds, that can modulate KIR2DL4 expression or activity. Having identified such a compound or composition, the active sites or regions are identified. Such active sites might typically be ligand-binding sites, such as the interaction domains of a ligand with KIR2DL4 itself. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the receptor the complexed ligand is found. Next, the three dimensional geometric structure of the active site is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures. The geometric structures may be measured with a complexed ligand, natural or artificial, which may increase the accuracy of the active site structure determined.

If an incomplete or insufficiently accurate structure is determined, the methods of computer based numerical modeling can be used to complete the structure or improve its accuracy. Any recognized modeling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential KIR2DL4 modulating compounds.

Alternatively, these methods can be used to identify improved modulating compounds from an already known modulating compound or ligand. The composition of the known compound can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Further experimental and computer modeling methods useful to identify modulating compounds based upon identification of the active sites of a ligand, KIR2DL4, and related transduction and transcription factors will be apparent to those of skill in the art.

Examples of molecular modeling systems are the CHARMM and QUANTA programs (Polygen Corporation, Waltham, Mass.). CHARMM performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific-proteins, such as Rotivinen, et al. 1988 *Acta Pharmaceutical Fennica* 97:159-166; Ripka, *New Scientist* 54-57 (Jun. 16, 1988); McKinaly and Rossmann 1989 *Annu Rev Pharmacol Toxicol* 29:111-122; Perry and Davies, *OSAR: Quantitative Structure-Activity Relationships in Drug Design* pp. 189-193 (Alan R. Liss, Inc. 1989); Lewis and Dean 1989 *Proc R Soc Lond* 236:125-140 and 141-162; and, with respect to a model receptor for nucleic acid components, Askew, et al. 1989 *J Am Chem Soc* 111: 1082-1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to regions of DNA or RNA, once that region is identified.

Although described above with reference to design and generation of compounds which could alter binding, one could also screen libraries of known compounds, including natural products or synthetic chemicals, and biologically active materials, including proteins, for compounds which are inhibitors or activators.

Compounds identified via assays such as those described herein may be useful, for example, in ameliorating infections, cancers, and autoimmune diseases. Assays for testing the effectiveness of compounds, identified by, for example, techniques such as those described will be discussed in the sections below.

In Vitro Screening Assays for Compounds that Bind to KIR2DL4

In vitro systems may be designed to identify compounds capable of interacting with (e.g., binding to) KIR2DL4. Compounds identified may be useful, for example, in modulating the activity of wild type and/or mutant KIR2DL4 gene products; may be useful in elaborating the biological function of KIR2DL4; may be utilized in screens for identifying compounds that modulate normal KIR2DL4 interactions; or may in themselves modulate such interactions.

The principle of the assays used to identify compounds that bind to KIR2DL4 involves preparing a reaction mixture of KIR2DL4 and the test compound under conditions and for a time sufficient to allow the two components to interact and bind, thus forming a complex which can be removed and/or detected in the reaction mixture. The KIR2DL4 species used can vary depending upon the goal of the screening assay. For example, where agonists of the natural ligand are sought, the full length KIR2DL4, or a soluble truncated KIR2DL4, a peptide corresponding to the extracellular domain or a fusion protein containing the KIR2DL4 extracellular domain fused to a protein or polypeptide that affords advantages in the assay system (e.g., labeling, isolation of the resulting complex, etc.) can be utilized. Where compounds that interact with the cytoplasmic domain are sought to be identified, peptides corresponding to the KIR2DL4 cytoplasmic domain and fusion proteins containing the KIR2DL4 cytoplasmic domain can be used.

The screening assays can be conducted in a variety of ways. For example, one method to conduct such an assay would involve anchoring the KIR2DL4 protein, polypeptide, peptide or fusion protein or the test substance onto a solid phase and detecting KIR2DL4/test compound complexes anchored on the solid phase at the end of the reaction. In one embodiment of such a method, the KIR2DL4 reactant may be anchored onto a solid surface, and the test compound, which is not anchored, may be labeled, either directly or indirectly.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for KIR2DL4 protein, polypeptide, peptide or fusion protein or the test compound to anchor any complexes formed in solution, and a labeled antibody specific for the other component of the possible complex to detect anchored complexes.

Alternatively, cell-based assays, membrane vesicle-based assays and membrane fraction-based assays can be used to identify compounds that interact with KIR2DL4. To this end, cell lines that express KIR2DL4, or cell lines (e.g., COS cells, CHO cells, fibroblasts, etc.) that have been genetically engineered to express KIR2DL4 (e.g., by transfection or transduction of KIR2DL4 DNA) can be used. Interaction of the test compound with, for example, the extracellular domain of KIR2DL4 expressed by the host cell can be determined by comparison or competition with a native ligand.

Assays for Intracellular or Other Proteins that Interact with the KIR2DL4

Any method suitable for detecting protein-protein interactions may be employed for identifying transmembrane proteins or intracellular proteins that interact with KIR2DL4. Among the traditional methods which may be employed are co-immunoprecipitation, crosslinking and co-purification through gradients or chromatographic columns of cell lysates or proteins obtained from cell lysates and KIR2DL4 to identify proteins in the lysate that interact with KIR2DL4. For these assays, the KIR2DL4 component used can be a full length KIR2DL4, a soluble derivative lacking the membrane-anchoring region, a peptide corresponding to the cytoplasmic domain or a fusion protein containing the cytoplasmic domain of KIR2DL4. Once isolated, such an intracellular protein can be identified and can, in turn, be used, in conjunction with standard techniques, to identify proteins with which it interacts. For example, at least a portion of the amino acid sequence of an intracellular protein which interacts with KIR2DL4 can be ascertained using techniques well known to those of skill in the art, such as via the Edman degradation technique. (See, e.g., Creighton, 1983, *Proteins: Structures and Molecular Principles,* W.H. Freeman & Co., N.Y., pp. 34-49). The amino acid sequence obtained may be used as a guide for the generation of oligonucleotide mixtures that can be used to screen for gene sequences encoding such intracellular proteins. Screening may be accomplished, for example, by standard hybridization or PCR techniques. Techniques for the generation of oligonucleotide mixtures and the screening are well-known. (See, e.g., Ausubel et al. 1989 *Current Protocols in Molecular Biology,* Green Publishing Associates and Wiley Interscience, N.Y.; and *PCR Protocols: A Guide to Methods and Applications,* 1990, Innis, M. et al., eds. Academic Press, Inc., New York).

Additionally, methods may be employed which result in the simultaneous identification of genes which encode the transmembrane or intracellular proteins interacting with KIR2DL4. These methods include, for example, probing expression libraries, in a manner similar to the well known technique of antibody probing of λgt11 libraries, using labeled KIR2DL4 protein, or a KIR2DL4 polypeptide, peptide or fusion protein, e.g., a KIR2DL4 polypeptide or KIR2DL4 domain fused to a marker (e.g., an enzyme, fluor, luminescent protein, or dye), or an Ig-Fc domain.

One method which detects protein interactions in vivo, the two-hybrid system, is described in detail for illustration only and not by way of limitation. One version of this system has been described (Chien et al. 1991 *PNAS* USA 88:9578-9582) and is commercially available from Clontech (Palo Alto, Calif.).

Briefly, utilizing such a system, plasmids are constructed that encode two hybrid proteins: one plasmid consists of nucleotides encoding the DNA-binding domain of a transcription activator protein fused to a KIR2DL4 nucleotide sequence encoding KIR2DL4, a KIR2DL4 polypeptide, peptide or fusion protein, and the other plasmid consists of nucleotides encoding the transcription activator protein's activation domain fused to a cDNA encoding an unknown protein which has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology may be used to screen activation domain libraries for proteins that interact with the "bait" gene product. By way of example, and not by way of limitation, KIR2DL4 may be used as the bait gene product. Total genomic or cDNA sequences are fused to the DNA encoding an activation domain. This library and a plasmid encoding a hybrid of a bait KIR2DL4 gene product fused to the DNA-binding domain are cotransformed into a yeast reporter strain, and the resulting transformants are screened for those that express the reporter gene. For example, a bait KIR2DL4 gene sequence, such as the open reading frame of KIR2DL4, can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait KIR2DL4 gene product are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait KIR2DL4 gene-GAL4 fusion plasmid into a yeast strain which contains a lacZ gene driven by a promoter which contains GAL4 activation sequence. A cDNA encoded protein, fused to GAL4 transcriptional activation domain, that interacts with bait KIR2DL4 gene product will reconstitute an active GAL4 protein and thereby drive expression of the HIS3 gene. Colonies which express HIS3 can be detected by their growth on petri dishes containing semi-solid agar based media lacking histidine. The cDNA can then be purified from these strains, and used to produce and isolate the bait KIR2DL4 gene-interacting protein using techniques routinely practiced in the art.

Assays for Compounds that Modulate the Interaction of Binding Partners with KIR2DL4

The macromolecules that interact with KIR2DL4 are referred to, for purposes of this discussion, as "binding partners". These binding partners are likely to be involved in the KIR2DL4 signal transduction pathway, and therefore, in the role of modulating interferon gamma production. Therefore, it is desirable to identify compounds that modulate the interaction of such binding partners with KIR2DL4 which can be useful in regulating the activity of KIR2DL4 and control effects associated with KIR2DL4 activity.

The basic principle of the assay systems used to identify compounds that modulate the interaction between KIR2DL4 and its binding partner or partners involves preparing a reaction mixture containing KIR2DL4 protein, polypeptide, peptide or fusion protein as described above, and the binding partner under conditions and for a time sufficient to allow the two to interact and bind, thus forming a complex. In order to test a compound for modulating activity, the reaction mixture is prepared in the presence and absence of the test compound. The test compound may be initially included in the reaction mixture, or may be added at a time subsequent to the addition of the KIR2DL4 moiety and its binding partner. Control reaction mixtures are incubated without the test compound or with a placebo. The formation of any complexes between the KIR2DL4 moiety and the binding partner is then detected. The formation of a complex in the control reaction, but not in the reaction mixture containing the test compound, indicates that the compound interferes with the interaction of KIR2DL4 and the interactive binding partner.

The assay for compounds that modulate the interaction of KIR2DL4 and binding partners can be conducted in a heterogeneous or homogeneous format. Heterogeneous assays involve anchoring either the KIR2DL4 moiety product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that inhibit interaction by competition can be identified by conducting the reaction in the presence of the test substance; i.e., by adding the test substance to the reaction mixture prior to or simultaneously with the KIR2DL4 moiety and interactive binding partner. Alternatively, test compounds that disrupt preformed complexes, e.g., compounds with higher binding constants that displace one of the components from the complex, can be tested by adding the test compound to the reaction mixture after complexes have been formed. The various formats are described briefly below.

In a heterogeneous assay system, either the KIR2DL4 moiety or the interactive binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the KIR2DL4 gene product or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the KIR2DL4 moiety and the interactive binding partner is prepared in which either KIR2DL4 or its binding partners is labeled, but the signal generated by the label is quenched due to formation of the complex (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt KIR2DL4/binding partner interaction can be identified.

In a particular embodiment, a KIR2DL4 fusion can be prepared for immobilization. For example, KIR2DL4 or a peptide fragment, can be fused to a glutathione-S-transferase (GST) gene using a fusion vector, such as pGEX-5X-1, in such a manner that its binding activity is maintained in the resulting fusion protein. The interactive binding partner can be purified and used to raise a monoclonal antibody, using methods routinely practiced in the art. This antibody can be labeled with the radioactive isotope $^{125}$I, for example, by methods routinely practiced in the art. In a heterogeneous assay, e.g., the GST-KIR2DL4 fusion protein can be anchored to glutathione-agarose beads. The interactive binding partner can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the KIR2DL4 gene product and the interactive binding partner can be detected by measuring the amount of radioactivity that remains associated with the glutathione-agarose beads. A successful inhibition of the interaction by the test compound will result in a decrease in measured radioactivity.

Alternatively, the GST-KIR2DL4 fusion protein and the interactive binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the KIR2DL4/binding partner interaction can be detected by adding the labeled antibody and measuring the radioactivity associated with the beads.

In another embodiment of the invention, these same techniques can be employed using peptide fragments that correspond to the binding domains of KIR2DL4 and/or the interactive or binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the binding partner is obtained, short gene segments can be engineered to express peptide fragments of the protein, which can then be tested for binding activity and purified or synthesized.

Assays for Identification of Compounds that Modulate Production of Interferon Gamma Compounds, including but not limited to binding compounds identified via assay techniques such as those described in the sections above can be tested for the ability to modulate the production of interferon gamma. The assays described above can identify compounds which affect KIR2DL4 activity, e.g., compounds that bind to the KIR2DL4, inhibit binding of the natural ligand, and either activate signal transduction (agonists) or block activation (antagonists), and compounds that bind to the natural ligand of KIR2DL4 and neutralize ligand activity. Such compounds can be used as part of a therapeutic regimen.

The invention encompasses cell-based and animal model-based assays for the identification of compounds exhibiting such an ability to modulate production of interferon gamma.

Cell-based systems, membrane vesicle-based systems and membrane fraction-based systems can be used to identify compounds which may act to modulate production of interferon gamma. Such cell systems can include, for example, recombinant or non-recombinant cells, such as cell lines, which express the KIR2DL4 gene. In addition, expression host cells (e.g., COS cells, CHO cells, fibroblasts) genetically engineered to express a functional KIR2DL4 and to respond to activation by a ligand, e.g., as measured by a chemical or phenotypic change, induction of another host cell gene, change in ion flux, tyrosine phosphorylation of host cell proteins, etc., can be used as an end point in the assay.

In addition, animal-based systems may be used to identify compounds capable of modulating production of interferon gamma. Such animal models may be used as test substrates for the identification of pharmaceuticals, therapies and interventions which may be effective in such modulation. KIR2DL4 is not expressed in mice, only in humans and chimps. Thus, chimp models are appropriate, as are transgenic mice genetically engineered to express KIR2DL4. For example, animal models may be exposed to a compound, suspected of exhibiting an ability to modulate production of interferon gamma, at a sufficient concentration and for a time sufficient to elicit such a modulation in the exposed animals. The response of the animals to the exposure may be monitored by assessing production of interferon gamma.

Pharmaceutical Preparations and Methods of Administration

The compounds that are determined to affect KIR2DL4 gene expression or KIR2DL4 activity can be administered to a patient at therapeutically effective doses to ameliorate disorders responsive to interferon gamma. A therapeutically effective dose refers to that amount of the compound sufficient to result in amelioration of symptoms of various types of infections, cancers and autoimmune diseases.

The pharmaceutical composition of the present invention is administered in vivo, ordinarily in a mammal, preferably in a human. In employing it in vivo, the pharmaceutical composition can be administered to a mammal in a variety of ways, including orally, parenterally, intravenously, subcutaneously, intramuscularly, colonically, rectally, nasally or intraperitoneally, employing a variety of dosage forms. Administration is preferably parenteral, such as intravenous on a daily basis. Alternatively, administration is preferably oral, such as by tablets, capsules or elixers taken on a daily basis.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

After pharmaceutical compositions have been prepared, they can be placed in an appropriate container and labeled for treatment of an indicated condition.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of cell lines, or in animal models. The animal model may also be used to determine the appropriate concentration range and route of administration. Such information can then be used to determine useful doses and routes for administration in humans.

A therapeutically effective dose refers to that amount of active ingredient, for example, antibodies or fragments thereof, agonists, antagonists or etc of KIR2DL4, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. For the present invention, alone or as part of a pharmaceutical composition, such doses are between about 0.01 mg/kg and 100 mg/kg body. weight, preferably between about 0.1 mg/kg and 10 mg/kg body weight.

The compositions may, if desired, be presented in a pack or dispenser device which may contain one or more unit dosage forms containing the active ingredient. The pack may or example comprise metal or plastic foil, such as a blister pack. The pack or dispenser device may be accompanied by instructions for administration.

While the present invention has been described in some detail for purposes of clarity and understanding, one skilled in the art will appreciate that various changes in form and detail can be made without departing from the true scope of the invention. All patents, patent applications and publications referred to above are hereby incorporated by reference.

What is claimed is:

1. A monoclonal antibody, mAb #33, produced by the hybridoma cell line having Accession No. ATCC PTA-2594.

2. A chimeric version of a monoclonal antibody, mAb #33, produced by the hybridoma cell line having Accession No. ATCC PTA-2594.

3. A humanized version of a monoclonal antibody, mAb #33, produced by the hybridoma cell line having Accession No. ATCC PTA-2594.

4. A Fab fragment of a monoclonal antibody, mAb #33, produced by the hybridoma cell line having Accession No. ATCC PTA-2594.

5. A F(ab')2 fragment of a monoclonal antibody, mAb #33, produced by the hybridoma cell line having Accession No. ATCC PTA-2594.

6. A hybridoma cell line having ATCC Accession No. PTA-2594.

7. A composition comprising the monoclonal antibody of claim 1 or a fragment or single chain antibody thereof that specifically binds to human KIR2DL4 receptor and stimulates production of interferon gamma.

8. A pharmaceutical composition comprising the monoclonal antibody of claim 1 or a fragment or single chain antibody thereof that specifically binds to human KIR2DL4 receptor and stimulates production of interferon gamma, and a pharmaceutically acceptable carrier.

9. The composition of claim 7 or 8, wherein said composition comprises said monoclonal antibody or said fragment.

10. The composition of claim 7 or 8, wherein said composition comprises said monoclonal antibody.

11. The composition of claim 7 or 8, wherein said composition comprises said single chain antibody.

12. A composition comprising the antibody of claim 2 or 3 that specifically binds to human KIR2DL4 receptor and stimulates production of interferon gamma.

13. The composition of claim 12, wherein said composition comprises said chimeric antibody.

14. The composition of claim 12, wherein said composition comprises said humanized antibody.

15. A pharmaceutical composition comprising the antibody of claim 2 or 3 that specifically binds to human KIR2DL4 receptor and stimulates production of interferon gamma, and a pharmaceutically acceptable carrier.

16. The pharmaceutical composition of claim 15, wherein said composition comprises said chimeric antibody.

17. The pharmaceutical composition of claim 15, wherein said composition comprises said humanized antibody.

* * * * *

SEQUENCE LISTING

```
<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: sense primer

<400> SEQUENCE: 1
ggggagatct cacgtgggtg gtcaggacaa                              30

<210> SEQ ID NO 2
<211> LENGTH: 37
<212> TYPE: DNA
<213> ORGANISM: Artificial Sequence
<220> FEATURE:
<223> OTHER INFORMATION: antisense primer

<400> SEQUENCE: 2
gactggtcga cgctagctca gattccagct gctggta                      37

<210> SEQ ID NO 3
<211> LENGTH: 30
<212> TYPE: DNA
<213> ORGANISM: Artificial Sequence
<220> FEATURE:
<223> OTHER INFORMATION: sense primer

<400> SEQUENCE: 3
catgctgtga ttgggacctc agtggccatc                              30

<210> SEQ ID NO 4
<211> LENGTH: 30
<212> TYPE: DNA
<213> ORGANISM: Artificial Sequence
<220> FEATURE:
<223> OTHER INFORMATION: antisense primer
```

```
<400> SEQUENCE: 4
gatggccact gaggtcccaa tcacagcatg                                         30
```